(12) United States Patent
Mirkin et al.

(10) Patent No.: US 8,323,686 B2
(45) Date of Patent: Dec. 4, 2012

(54) NANOSTRUCTURES SUITABLE FOR SEQUESTERING CHOLESTEROL AND OTHER MOLECULES

(75) Inventors: Chad A. Mirkin, Wilmette, IL (US); C. Shad Thaxton, Chicago, IL (US); David A. Giljohann, Chicago, IL (US); Weston Daniel, Evanston, IL (US)

(73) Assignee: Northwestern University, Evanston, IL (US)

( * ) Notice: Subject to any disclaimer, the term of this patent is extended or adjusted under 35 U.S.C. 154(b) by 469 days.

(21) Appl. No.: 12/429,560

(22) Filed: Apr. 24, 2009

(65) Prior Publication Data

US 2011/0059156 A9  Mar. 10, 2011

Related U.S. Application Data

(60) Provisional application No. 61/047,903, filed on Apr. 25, 2008, provisional application No. 61/098,923, filed on Sep. 22, 2008, provisional application No. 61/117,350, filed on Nov. 24, 2008, provisional application No. 61/160,165, filed on Mar. 13, 2009.

(51) Int. Cl.
*A61K 9/127* (2006.01)
*A61K 9/14* (2006.01)

(52) U.S. Cl. ........ 424/450; 424/489; 977/702; 977/713; 977/907

(58) Field of Classification Search ................... None
See application file for complete search history.

(56) References Cited

U.S. PATENT DOCUMENTS

| 6,274,337 | B1 | 8/2001 | Parce et al. |
| 7,691,414 | B2 | 4/2010 | Sligar et al. |
| 2004/0053384 | A1 | 3/2004 | Sligar et al. |
| 2006/0292174 | A1 | 12/2006 | De Los Rios et al. |
| 2007/0243136 | A1 | 10/2007 | Fisher et al. |

FOREIGN PATENT DOCUMENTS

| CN | 1474831 A | 2/2004 |
| WO | WO 93/21528 A1 | 10/1993 |
| WO | WO 2007/089607 A2 | 8/2007 |
| WO | WO 2008/106660 A2 | 9/2008 |
| WO | WO 2008/141230 A1 | 11/2008 |

OTHER PUBLICATIONS

Matsunaga, et al. (1998) "Biomagnetic Nanoparticle Formation and Application", Supramolecular Science, 5(3-4): 391-94.*
Senarath-Yapa, et al. (Nov. 2, 2007) "Preparation and Characterization of Poly(lipid)-coated, Fluorophore-Doped Silica Nanoparticles for Biolabeling and Cellular Imaging", Langmuir, 23(25): 12624-33.*
Chinese Office Action for CN 200980118614.7 dated Aug. 23, 2011.
Chromy, B. et al. "Different Apolipoproteins Impact Nanolipoprotein Particle Formation" J. Am. Chem. Soc., 2007, 129, 14348-14354.
Cormode, D.P. et al., "Nanocrystal Core High-Density Lipoproteins: A Multimodality Contrast Agent Platform," *Nano Letters*, 2008, 8 (11), 3715-3723.
Elbakry, A. et al. "Layer-by-Layer Assembled Gold Nanoparticles for siRNA Delivery" Nano Letters, 2009, vol. 9, No. 5, 2059-2064.
Fan, H. et al., "Self-Assembly of Order, Robust, Three-Dimensional Gold Nanocrystal/Silica Arrays," *Science*, 2004, 403, 567-571.
Frias, J. C. et al., "Properties of a Versatile Nanoparticle Platform Contrast Agent to Image and Characterize Atherosclerotic Plaques by Magnetic Resonance Imaging," Nano Letters, 2006, 6 (10), 2220-2224.
Frias, J. C. et al., " Recombinant HDL-Like Nanoparticles: A Specific Contrast Agent for MRI of Atherosclerotic Plaques," *J. Am. Chem. Sos.*, 2004, 126 (50), 16316-16317.
He, P. et al. "Phospholipid-Stabilized Au—Nanoparticles" Biomacromolecules 2005, 6, 1224-1225.
Hurst, S. et al. "Maximizing DNA loading on a range of gold nanoparticle sizes" Analytical Chemistry, American Chemical Society, US, vol. 78, No. 24, Dec. 15, 2006, pp. 8313-8318.
Leander, D. "Mixed-Monolayer Gold Nanoparticles for Cancer Therapeutics" Nanoscape, vol. 7, issue 1, Sep. 2010, pp. 11-14.
Liu, J. et al. "Silica nanoparticle supported lipid bilayers for gene delivery" Chem. Commun , 2009, 5100-5102.
Major, M. et al. "Characterisation and phase behaviour of phospholipid bilayers adsorbed on spherical polysaccharidic nanoparticles" Biochemica et Biophysica Acta 1327 (1997) 32-40.
McBain, S. et al. "Polyethyleneimine functionalized iron oxide nanoparticles as agents for DNA deliver and transfection" Journal of Materials Chemistry, 2007, 17, 2561-2565.
Mukherjee, S. et al. "Monitoring cholesterol organization in membranes at low concentrations utilizing the wavelength-selective fluorescence approach" Chemistry and Physics of Lipids, Limerick, IR, vol. 134, No. 1, Mar. 1, 2005.
Niemeyer, C. et al. "Bifunctional DNA-gold nanoparticle conjugates as building blocks for the self-assembly of cross-linked particle layers" Biochemical and Biophysical Research Communications, Academic Press Inc. Orlando, FL, US, vol. 311, No. 4, Nov. 28, 2003, pp. 995-999.

(Continued)

*Primary Examiner* — Robert M Kelly
(74) *Attorney, Agent, or Firm* — Wolf, Greenfield & Sacks, P.C.

(57) ABSTRACT

Articles, compositions, kits and methods relating to nanostructures, including those that can sequester molecules such as cholesterol, are provided. Certain embodiments described herein include structures having a core-shell type arrangement; for instance, a nanoparticle core may be surrounded by a shell including a material, such as a lipid bilayer, that can interact with cholesterol and/or other lipids, and an apolipoprotein may be bound to at least the outer surface of the shell. In some embodiments, the structures, when introduced to a subject, can sequester cholesterol and/or other lipids and remove them from circulation. Accordingly, the structures described herein may be used to diagnose, prevent, treat or manage certain diseases or bodily conditions, especially those associated with abnormal lipid levels.

45 Claims, 14 Drawing Sheets

OTHER PUBLICATIONS

Patile, V. et al., "Evidence for Novel Interdigitated Bilayer Formation of Fatty Acids during Three-Dimensional Self-Assembly on Silver Colloidal Particles," *J. Am. Chem. Sos.*, 1997, 119, 9281-9282.

Raj, S. et al. "Enhanced Gene and siRNA Delivery by Polycation-Modified Mesoporous Silica Nanoparticles Loaded with Chloroquine" Pharm Res (2010) 27:2556-2568.

Takahashi, H. et al., "Modification of Gold Nanorods Using Phosphatidylcholine to Reduce Cytotoxicity," Langmuir, 2006, 22, 2-5.

Thaxton, C.S. et al., Templated Spherical High Density Lipoprotein Nanoparticles, *J. Am. Chem. Sos.*, 2009, 131, 1384-1385.

Xia, T. et al., "Polyethyleneimine Coating Enhances the Cellular Uptake of Mesoporous Silica Nanoparticles and Allows Safe Delivery of siRNA and DNA Constructs", ACSNANO, vol. 3, No. 10, 3273-3286, 2009.

Zhang et al. "A sensitive impedance immunosensor based on functionalized gold nanoparticle-protein composite films for probing apol,ipoprotein A-I" Talanta, Elsevier, Amsterdam, NL, vol. 71, No. 2, Jan. 20, 2007, pp. 874-881.

International Search Report and Written Opinion from PCT/US2009/002540 dated Jul. 7, 2010.

* cited by examiner 1,2-Dipalmitoyl-*sn*-Glycero-3-Phosphothioethanol (SH-lipid)

L-alpha Phosphatidylcholine (N+-lipid)

NANOSTRUCTURES SUITABLE FOR SEQUESTERING CHOLESTEROL AND OTHER MOLECULES

RELATED APPLICATIONS

This application claims the benefit of U.S. Provisional Patent Application Ser. No. 61/047,903, filed Apr. 25, 2008, entitled "Nanoparticle Supported Lipid Functionalized Bio-Mimetic Structures"; U.S. Provisional Patent Application Ser. No. 61/098,923, filed Sep. 22, 2008, entitled "Nanoparticle Supported Lipid Bi-Layer Bio-Mimetic Structures"; U.S. Provisional Patent Application Ser. No. 61/117,350, filed Nov. 24, 2008, entitled "Templated Spherical High Density Lipoprotein Nanoparticles"; and U.S. Provisional Patent Application Ser. No. 61/160,165, filed Mar. 13, 2009, entitled "Nanostructures Suitable for Sequestering Cholesterol and Other Molecules"; each of which is incorporated herein by reference in its entirety for all purposes.

FEDERALLY SPONSORED RESEARCH

This invention was made with U.S. government support under NIH (NCI/CCNE) grant No. U54 CA 119341 and NIH Pioneer Award No. 5 DP1 OD000285. The government has certain rights to this invention.

FIELD OF INVENTION

The present invention relates generally to methods for fabricating nanostructures including articles and compositions thereof, and more specifically, to nanostructures that can sequester molecules such as cholesterol.

BACKGROUND

Nanostructures, including liposome nanostructures, are currently being used in applications such as drug delivery, gene delivery, and diagnostics. A variety of methods have been used to fabricate such nanostructures; for example, liposome nanostructures have been formed by techniques including lipoprotein/conjugate synthesis and sonicating mixtures of amphipathic liposome components. However, some such methods often lead to structures having relatively large sizes, large size distributions, and/or short term stability. Accordingly, a need exists for nanostructures having smaller sizes, controlled size distributions, and/or long term stability, and methods for making such nanostructures, while being able to control functionality and tailorability of the nanostructures.

SUMMARY OF THE INVENTION

The present invention generally relates to nanostructures and compositions for diagnosing, preventing, treating or managing certain diseases or bodily conditions, including those associated with abnormal lipid levels. Accordingly, certain embodiments described herein are arranged to sequester lipids such as cholesterol. The subject matter of this application involves, in some cases, interrelated products, alternative solutions to a particular problem, and/or a plurality of different uses of structures and compositions.

In one set of embodiments, a structure is provided. In one embodiment, a structure includes a nanostructure core comprising an inorganic material, and a shell comprising a lipid bilayer surrounding and attached to the nanostructure core. The shell has an inner surface and an outer surface, and a protein is associated with at least the outer surface of the shell. The structure may be adapted to sequester cholesterol (or other lipids or molecules in certain embodiments).

In another embodiment, a structure includes a nanostructure core having a largest cross-sectional dimension of less than or equal to about 30 nm, and a shell comprising a lipid bilayer surrounding and attached to the nanostructure core. The shell has an inner surface and an outer surface, and a protein associated with at least the outer surface of the shell. The structure may be adapted to sequester cholesterol (or other lipids or molecules in certain embodiments).

In the structures described above and herein, the lipid bilayer may include one or more phospholipids, e.g., 50-200 phospholipids. The shell may have a lipoprotein structure, and may optionally include an apolipoprotein, e.g., apolipoprotein A-I, apolipoprotein A-II, or apolipoprotein E.

In another set of embodiments, a pharmaceutical composition is provided. A pharmaceutical composition may include a structure comprising a nanostructure core comprising an inorganic material and a shell surrounding and attached to the nanostructure core. The structure may be adapted to sequester cholesterol (or other lipids or molecules in certain embodiments). The pharmaceutical composition may also include one or more pharmaceutically acceptable carriers, additives, and/or diluents. The structure of the composition may include a shell that comprises a lipid, and in some embodiments, a lipid bilayer. One or more proteins may be associated with at least the outer surface of the shell. The nanostructure core may, in some cases, include an inorganic material.

In another set of embodiments, a kit for diagnosing, preventing, treating or managing a disease or bodily condition associated with abnormal lipid levels is provided. The kit can include a composition comprising a plurality of structures, each structure comprising a nanostructure core comprising an inorganic material and a shell surrounding and attached to the nanostructure core. The structure may be adapted to sequester cholesterol (or other lipids or molecules in certain embodiments). The kit also includes instructions for use of the composition for diagnosing, preventing, treating or managing a disease or bodily condition associated with abnormal lipid levels. The kit may be used for diagnosing, preventing, treating or managing a disease or bodily condition associated with abnormally high lipid levels or abnormally low lipid levels, or for diagnosing, preventing, treating or managing a cardiovascular disease, atherosclerosis, hyperlipidemia, cancer, inflammation, a protein storage disease, a disease of hemostasis, a rheumatic disease, or a neurologic disease.

In another set of embodiments, a series of methods are provided. In one embodiment, a method for diagnosing, preventing, treating or managing a disease or bodily condition associated with abnormal lipid levels is provided. The methods involves administering to a subject a therapeutically-effective amount of a composition comprising a structure comprising a nanostructure core comprising an inorganic material and a shell surrounding and attached to the nanostructure core. The structure may be adapted to sequester cholesterol (or other lipids or molecules in certain embodiments). The method may include allowing the structure to sequester cholesterol, e.g., at least 5, 20, or 50 molecules of cholesterol. The cholesterol may be, for example, esterified cholesterol or free cholesterol. In other embodiments, a method involves allowing the structure to sequester molecules of a particular type or composition, e.g., at least 5, 20, or 50 molecules of a particular type or composition.

In another embodiment, a method involves introducing a composition comprising a plurality of structures to a subject or a biological sample, each structure comprising a nanostructure core comprising an inorganic material and a shell surrounding and attached to the nanostructure core. The structure may be adapted to sequester cholesterol (or other lipids or molecules in certain embodiments). The method also involves exposing the plurality of structures and/or the subject or biological sample to testing conditions that can determine a disease or condition of the subject or biological sample. For example, the testing conditions may be imaging conditions. In other cases, the testing conditions are assay conditions, the method includes retrieving at least a portion of the plurality of structures from the subject or biological sample and performing an assay with the plurality of structures retrieved from the subject or biological sample.

In another embodiment, a method involves providing a nanostructure core having a surface and a largest cross-sectional dimension of less than or equal to about 50 nm, providing a plurality of components, and forming a layer of the plurality of components on the surface of the nanostructure core by self-assembly, wherein the plurality of components surround the nanostructure core. The method may also include removing at least a portion of the nanostructure core, and forming a structure comprising the plurality of components surrounding an at least partially hollow core. Optionally, the method may involve crosslinking the plurality of components on the surface of the nanostructure core prior to (or before) the removing step.

In another embodiment, a method involves combining a plurality of first components, a plurality of second components, and a plurality of nanostructure cores in a single phase of a liquid. The method also involves forming, by self-assembly, a first layer comprising the plurality of first components on a surface of at least one nanostructure core, and forming, by self-assembly, a second layer comprising the plurality of second components adjacent the first layer. The first and second layers constitute a shell surrounding the at least one nanostructure core.

In certain embodiments described above and herein, the shell substantially surrounds the nanostructure core.

The present invention also relates to the use of any of the compositions and/or structures described above in the preparation of a medicament for diagnosing, preventing, treating or managing certain diseases or bodily conditions, especially those associated with abnormal lipid levels.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 9B and 9C are TEM images showing gold nanoparticles functionalized with $C_{10}$ lipids according to one set of embodiments;

FIGS. 9E and 9F are TEM images showing gold nanoparticles functionalized with $C_{10}$ lipids and Apo-AI, according to one set of embodiments;

DETAILED DESCRIPTION

Figure 1:
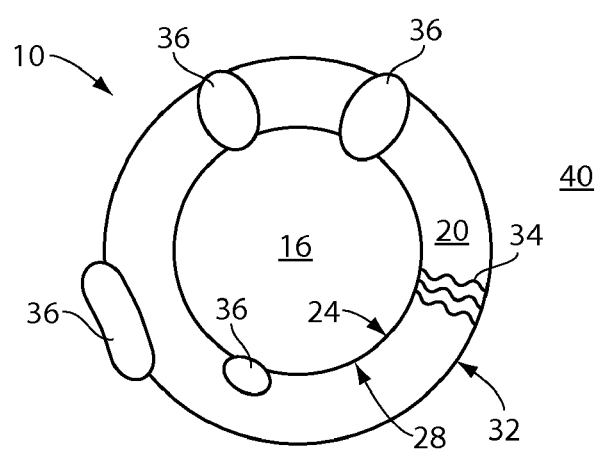
FIG. 1 shows an example of a structure that can be used to sequester cholesterol according to one set of embodiments.

Articles, compositions, kits, and methods relating to nanostructures, including those that can sequester molecules such as cholesterol, are provided. Certain embodiments described herein include structures having a core-shell type arrangement; for instance, a nanoparticle core may be surrounded by a shell including a material, such as a lipid bilayer, that can interact with cholesterol and/or other lipids. In some embodiments, the structures, when introduced into a subject, can sequester cholesterol and/or other lipids and remove them from circulation. Accordingly, the structures described herein may be used to diagnose, prevent, treat or manage certain diseases or bodily conditions, especially those associated with abnormal lipid levels.

Certain structures described herein can mimic circulating lipoproteins such as high density lipoprotein (HDL) and low density lipoprotein (LDL), commonly referred to as "good" and "bad" cholesterol, respectively. One function of lipoproteins is to transport cholesterol and other lipids in the body in the aqueous blood, since these molecules do not normally dissolve in the blood. Lipoproteins are also responsible for a number of important pathologic functions such as atherosclerosis. These lipoproteins, and other similar circulating particles (e.g., intermediate density lipoproteins, very low density lipoproteins, etc.), include nanostructures typically between 5 and 1000 nm. Each lipoprotein is unique with regard to its surface chemistry, size and composition. However, they also have in common an outer layer of phospholipids, an inner core of hydrophobic moieties (e.g., cholesteryl esters and triglycerides), and a surface protein that identifies individual lipoprotein species and dictates physiology.

In some embodiments described herein, a core (e.g., a gold nanoparticle) can be used as a scaffold to template and direct the synthesis of structures of well defined size, shape, and surface chemistry that are amenable to a wide variety of further surface chemistry and tailorability. For example, a bottom-up, size-specific, lipoprotein synthesis may be carried out by using a nanostructure core to support a shell including a lipid bilayer and/or other suitable components. To the knowledge of the inventors, biologically relevant lipid structures with tailorable and expanded surface chemistries (e.g., protein immobilization), especially those that can sequester cholesterol, have not been demonstrated, e.g., in the context of inorganic nanostructures, wherein the nanostructures act to restrict and template the size of formed structures. Furthermore, the inventors believe that there are currently no examples of structures such as synthetic lipid (or lipoprotein) species (with or without nanostructure cores) in the 5-30 nm, or even 5-50 nm, size regime that are capable of sequestering cholesterol and/or use as therapeutic agents, where one is able to control the size and shape of the structures, while having the ability to chemically tailor the core and/or surface properties to derive further therapeutic or other benefit.

Certain previous attempts at synthesizing and/or reconstitute synthetic lipoproteins, especially HDL, rely upon purification of surface identifying protein species, which are responsible for the self assembly of the lipoprotein, and mixing with constituent phospholipids, cholesterol, and other components. Vigorous mixing of these particles results in a solution filled with reconstituted lipoprotein species and numerous by-products of the reaction. Accordingly, some such preparations have limited shelf life due to instability; are limited as therapeutic agents by their short in vivo circulation times due to particle instability; and are quite expensive to make as they rely upon the availability of pure lipoprotein constituent protein species for assembly. In contrast, certain articles and methods described herein involve the use of nanostructure scaffolds for controllable synthesis of structures with a high degree of reproducibility and with the potential for massive scale-up. The resulting structures may be stable in a variety of solvents, may have high in vivo circulation times, and may be relatively inexpensive to fabricate. Additionally, as lipids can be easily modified with commercially available linker chemistries, the structures described herein are amenable to further functionalization with potential pharmacological agents and/or targeting/recognition agents such as antibodies, small molecules and proteins. Further advantages are described in more detail below.

Examples of inventive structures are now described.

The illustrative embodiment of FIG. 1 includes a structure 10 having a core 16 and a shell 20 surrounding the core. In embodiments in which the core is a nanostructure, the core includes a surface 24 to which one or more components can be optionally attached. For instance, in some cases, core 16 is a nanostructure surrounded by shell 20, which includes an inner surface 28 and an outer surface 32. The shell may be formed, at least in part, of one or more components 34, such as a plurality of lipids, which may optionally associate with one another and/or with surface 24 of the core. For example, components 34 may be associated with the core by being covalently attached to the core, physisorbed, chemisorbed, or attached to the core through ionic interactions, hydrophobic and/or hydrophilic interactions, electrostatic interactions, van der Waals interactions, or combinations thereof. In one particular embodiment, the core includes a gold nanostructure and the shell is attached to the core through a gold-thiol bond.

Optionally, components 34 can be crosslinked to one another. Crosslinking of components of a shell can, for example, allow the control of transport of species into the shell, or between an area exterior to the shell and an area interior of the shell. For example, relatively high amounts of crosslinking may allow certain small, but not large, molecules to pass into or through the shell, whereas relatively low or no crosslinking can allow larger molecules to pass into or through the shell. Additionally, the components forming the shell may be in the form of a monolayer or a multilayer, which can also facilitate or impede the transport or sequestering of molecules. In one exemplary embodiment, shell 20 includes a lipid bilayer that is arranged to sequester cholesterol, as described in more detail below.

It should be understood that a shell which surrounds a core need not completely surround the core, although such embodiments may be possible. For example, the shell may surround at least 50%, at least 60%, at least 70%, at least 80%, at least 90%, or at least 99% of the surface area of a core. In some cases, the shell substantially surrounds a core. In other cases, the shell completely surrounds a core. The components of the shell may be distributed evenly across a surface of the core in some cases, and unevenly in other cases. For example, the shell may include portions (e.g., holes) that do not include any material in some cases. If desired, the shell may be designed to allow penetration and/or transport of certain molecules and components into or out of the shell, but may prevent penetration and/or transport of other molecules and components into or out of the shell. The ability of certain molecules to penetrate and/or be transported into and/or across a shell may depend on, for example, the packing density of the components forming the shell and the chemical and physical properties of the components forming the shell. As described herein, the shell may include one layer of material, or multilayers of materials in some embodiments.

Structure 10 may also include one or more components 36 such as proteins, nucleic acids, and bioactive agents which may optionally impart specificity to the structure. One or more components 36 may be associated with the core, the shell, or both; e.g., they may be associated with surface 24 of the core, inner surface 28 of the shell, outer surface 32 of the shell, and/or embedded in the shell. For example, one or more components 36 may be associated with the core, the shell, or both through covalent bonds, physisorption, chemisorption, or attached through ionic interactions, hydrophobic and/or hydrophilic interactions, electrostatic interactions, van der Waals interactions, or combinations thereof. In one particular embodiment, shell 20 is in the form of a lipoprotein assembly or structure which includes both proteins and lipids that are covalently or non-covalently bound to one another. For example, the shell may be in the form of an apolipoprotein assembly that serves as an enzyme co-factor, receptor ligand, and/or lipid transfer carrier that regulates the uptake of lipids. As described herein, the components of structure 10 may be chosen such that the surface of the structure mimics the general surface composition of HDL, LDL, or other structures.

It should be understood that components and configurations other than those described herein may be suitable for certain structures and compositions, and that not all of the components shown in FIG. 1 are necessarily present in some embodiments.

In some cases, core 16 is hollow and therefore does not include a nanostructure core. Thus, in some such and other embodiments, structure 10 includes a shell that can optionally allow components (e.g., bioactive agents, cholesterol) to pass to and from core 16 and an environment 40 outside of the shell. In contrast to certain existing hollow structures (e.g., liposomes) which typically have a largest cross-sectional dimension of greater than about 100 nm due to the steric hindrance of the components forming the shell, structures 10 having a hollow core (e.g., a partially or wholly hollow core) may be very small, e.g., having a largest cross-sectional dimension of less than about 100 nm, or even less than about 50 nm. For example, liposomes that include a lipid bilayer comprising phospholipids are difficult to fabricate having a size of less than 100 nm since the phospholipids become limited sterically, thus making it difficult or impossible to form bilayered hollow structures with small radii of curvature. Using the methods described herein, however, such and other structures having small radii of curvature can be formed, as provided in more detail below.

In one set of embodiments, structure 10, whether including a nanostructure core or a hollow core, is constructed and arranged to sequester, transport, or exchange certain molecules to and/or from a subject or a biological sample. For instance, structure 10, when introduced into a subject, may interact with one or more components in the subject such as cells, tissues, organs, particles, fluids (e.g., blood), and portions thereof. The interaction may take place, at least in part, through the shell of structure 10, and may involve, for example, the exchange of materials (e.g., proteins, peptides, polypeptides, nucleic acids, nutrients) from the one or more components of the subject to structure 10, and/or from structure 10 to the one or more components of the subject. In some such embodiments, the shell of structure 10 can be designed to include components with properties that allow favorable interaction (e.g., binding, adsorption, transport) with the one or more materials from the subject. For example, the shell may include components having a certain hydrophobicity, hydrophilicity, surface charge, functional group, specificity for binding, and/or density to facilitate particular interactions, as described in more detail below. In certain embodiments, one or more materials from a subject are sequestered by structure 10, and structure 10 facilitates excretion, breakdown, and/or transport of the material. The excretion, breakdown, and/or transport of the material can lead to certain beneficial and/or therapeutic effects. As such, the structures described herein can be used for the diagnosis, prevention, treatment or management of certain diseases or bodily conditions.

In one particular set of embodiments, structure 10, whether including a nanostructure core or a hollow core, is constructed and arranged to sequester cholesterol (and/or other lipids). Without wishing to be bound by theory, it is hypothesized that structure 10 sequesters cholesterol through hydrophobic interactions with a hydrophobic layer (e.g., a lipid bilayer) of the structure. For example, in some cases, cholesterol can bind to a surface of the structure (e.g., to the outer surface of the shell) through hydrophobic interactions. In other cases, the cholesterol can be transported from an outer surface of the shell to an inner surface of the shell and/or to the core of the structure. The cholesterol can also be imbedded in the shell, e.g., between two layers of the shell. Optionally, structure 10 may include one or more apolipoproteins (e.g., apoliprotein-A1), proteins, or peptides, which can facilitate the sequestering of cholesterol. Structure 10 may also sequester cholesterol by removing cholesterol and phospholipids from a cell, or from other circulating lipoprotein species. Cholesterol sequestered by structure 10 may be esterified enzymatically (e.g., by lecithin:acyl CoA transferase (LCAT)) to form a cholesteryl ester that may migrate towards the center of the structure. In the case of hollow core embodiments, the cholesteryl ester may accumulate in the hollow core.

Additionally, without wishing to be bound by theory, it is believed that the structures described herein can sequester cholesterol from high concentrations of cholesterol (e.g., plaques) and transfer it to the liver directly or indirectly. For example, cholesterol may be sequestered from areas of high concentrations of cholesterol (e.g., plaques) by direct efflux of cholesterol from the plaque, or any components of the plaque, into or onto the structures described herein. In some such embodiments, the cholesterol that is sequestered by the structures is transported directly to the liver by the structures. In other embodiments, other circulating lipoprotein species (e.g., LDL) may participate in cholesterol exchange. For example, in some cases, free cholesterol or esterified cholesterol is transferred from other lipoproteins to the structures described herein. In other cases, once free cholesterol or esterified cholesterol is sequestered by the structures described herein, the cholesterol can be transferred from the structures to the other lipoprotein species, which may ultimately end up in the liver. Thus, in such embodiments, the structures described herein can augment reverse cholesterol transport indirectly. Furthermore, in the case where free cholesterol or esterified cholesterol is sequestered from the structures described herein to other lipoprotein species, the structures may further sequester cholesterol from, for example, areas of high cholesterol content, plaques, circulating lipoproteins, or other physiologic sites of high cholesterol concentration. It should be understood, however, that the structures described herein may remove cholesterol and/or other molecules by other routes, such as through urine, and the invention is not limited in this respect.

Accordingly, structures 10 may be used in the field of cardiovascular disease for studying atherosclerosis and cholesterol transport, and, generally, to diagnose, prevent, treat or manage diseases or bodily conditions associated with abnormal lipid levels, as described in more detail below.

The amount of a molecule (e.g., cholesterol or other lipids) sequestered by a structure and/or a composition described herein may depend on, for example, the size of the structure, the biology and surface chemistry of the particle, as well as the method of administration. For instance, if the structures are circulated indefinitely from the periphery to the liver and out again, relative few cholesterol molecules need to be sequestered by each structure in order for the composition to be effective, since the structures are recycled. On the other hand, if a composition is used, for example, as a cholesterol or bile-salt binding resin orally, each structure may sequester a larger number of cholesterol to increased cholesterol uptake. Also, if the structures are of a size such that they are rapidly excreted (e.g., through the liver or urine) after sequestering cholesterol, a high uptake of cholesterol per structure, and/or continuous infusion may be implemented. As such, a single structure described herein, which may be incorporated into a pharmaceutical composition or other formulation, may be able to sequester any suitable number of a particular type of molecule (e.g., lipids such as cholesterol; steroids such as estrogen, progesterone, and testosterone; bile salts, etc.) during use, e.g., at least 2, at least 5, at least 10, at least 20, at least 30, at least 50, at least 100, at least 200, at least 500, at least 1,000, at least 2,000, at least 5,000, or at least 10,000 molecules, which may depend on the size (e.g., surface area and/or volume) of the structure, the particular application, and the method of administration. In some cases, such numbers of molecules can be bound to the structure at one particular instance.

In some cases, a single structure has a binding constant for cholesterol, $K_d$, of, for example, less than or equal to about 100 µM, less than or equal to about 10 µM, less than or equal to about 1 µM, less than or equal to about 0.1 µM, less than or equal to about 10 nM, less than or equal to about 7 nM, less than or equal to about 5 nM, less than or equal to about 2 nM, less than or equal to about 1 nM, less than or equal to about 0.1 nM, less than or equal to about 10 µM, less than or equal to about 1 µM, less than or equal to about 0.1 µM, less than or equal to about 10 fM, or less than or equal to about 1 fM. Methods for determining the amount of cholesterol sequestered and binding constants are provided in more detail below.

In certain embodiments, the molecules that are sequestered by the structures described herein cause the structure to grow in size (e.g., cross-sectional area, surface area and/or volume), e.g., depending on the number of molecules sequestered. The molecules may associate with a surface of a structure, be imbedded in a shell of a structure, be transported to a core of the structure, or combinations thereof, as described herein. As such, the size of a structure (e.g., cross-sectional area, surface area and/or volume) can increase by at least 5%, at least 10%, at least 20%, at least 30%, at least 50%, at least 70%, or at least 100%, from a time prior to sequestration compared to a time after/during sequestration in some embodiments.

It should be understood, however, that while many of the embodiments herein are described in the context of sequestering cholesterol or other lipids, the invention is not limited as such and the structures, compositions, kits, and methods described herein may be used to sequester other molecules and/or to prevent, treat, or manage other diseases or bodily conditions.

Core 16, whether being a nanostructure core or a hollow core, may have any suitable shape and/or size. For instance, the core may be substantially spherical, non-spherical, oval, rod-shaped, pyramidal, cube-like, disk-shaped, wire-like, or irregularly shaped. The core (e.g., a nanostructure core or a hollow core) may have a largest cross-sectional dimension (or, sometimes, a smallest cross-section dimension) of, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, the core has an aspect ratio of greater than about 1:1, greater than 3:1, or greater than 5:1. As used herein, "aspect ratio" refers to the ratio of a length to a width, where length and width measured perpendicular to one another, and the length refers to the longest linearly measured dimension.

In embodiments in which core 16 includes a nanostructure core, the nanostructure core may be formed from any suitable material. For instance, in one embodiment, a nanostructure core comprises an inorganic material. The inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least 1 wt %, 5 wt %, 10 wt %, 25 wt %, 50 wt %, 75 wt %, 90 wt %, or 99 wt %. In one embodiment, the core is formed of 100 wt % inorganic material. The nanostructure core may, in some cases, be in the form of a quantum dot, a carbon nanotube, a carbon nanowire, or a carbon nanorod. In some cases, the nanostructure core comprises, or is formed of, a material that is not of biological origin. In some embodiments, a nanostructure includes one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen.

Structure 10, which may include a shell 20 surrounding core 16, may also have any suitable shape and/or size. For instance, a structure may have a shape that is substantially spherical, oval, rod-shaped, pyramidal, cubed-like, disk-shaped, or irregularly shaped. The largest cross-sectional dimension (or, sometimes, a smallest cross-section dimension) of a structure may be, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. The structure may also have an aspect ratio substantially similar to the aspect ratio of the core.

Furthermore, a shell of a structure can have any suitable thickness. For example, the thickness of a shell may be at least 10 Angstroms, at least 0.1 nm, at least 1 nm, at least 2 nm, at least 5 nm, at least 7 nm, at least 10 nm, at least 15 nm, at least 20 nm, at least 30 nm, at least 50 nm, at least 100 nm, or at least 200 nm (e.g., from the inner surface to the outer surface of the shell). In some cases, the thickness of a shell is less than 200 nm, less than 100 nm, less than 50 nm, less than 30 nm, less than 20 nm, less than 15 nm, less than 10 nm, less than 7 nm, less than 5 nm, less than 3 nm, less than 2 nm, or less than 1 nm (e.g., from the inner surface to the outer surface of the shell). Such thicknesses may be determined prior to or after sequestration of molecules as described herein.

Those of ordinary skill in the art are familiar with techniques to determine sizes of structures and particles. Examples of suitable techniques include dynamic light scattering (DLS) (e.g., using a Malvern Zetasizer instrument), transmission electron microscopy, scanning electron microscopy, electroresistance counting and laser diffraction. Other suitable techniques are known to those or ordinary skill in the art. Although many methods for determining sizes of nanostructures are known, the sizes described herein (e.g., largest or smallest cross-sectional dimensions, thicknesses) refer to ones measured by dynamic light scattering.

The shell of a structure described herein may comprise any suitable material, such as a hydrophobic material, a hydrophilic material, and/or an amphiphilic material. Although the shell may include one or more inorganic materials such as those listed above for the nanostructure core, in many embodiments the shell includes an organic material such as a lipid or certain polymers. The components of the shell may be chosen, in some embodiments, to facilitate the sequestering of cholesterol or other molecules. For instance, cholesterol (or other sequestered molecules) may bind or otherwise associate with a surface of the shell, or the shell may include components that allow the cholesterol to be internalized by the structure. Cholesterol (or other sequestered molecules) may also be embedded in a shell, within a layer or between two layers forming the shell. The components of a shell may be charged, e.g., to impart a charge on the surface of the structure, or uncharged.

In one set of embodiments, a structure described herein or a portion thereof, such as a shell of a structure, includes one or more natural or synthetic lipids or lipid analogs (i.e., lipophilic molecules). One or more lipids and/or lipid analogues may form a single layer or a multi-layer (e.g., a bilayer) of a structure. In some instances where multi-layers are formed, the natural or synthetic lipids or lipid analogs interdigitate (e.g., between different layers). Non-limiting examples of natural or synthetic lipids or lipid analogs include fatty acyls, glycerolipids, glycerophospholipids, sphingolipids, saccharolipids and polyketides (derived from condensation of ketoacyl subunits), and sterol lipids and prenol lipids (derived from condensation of isoprene subunits).

In one particular set of embodiments, a structure described herein includes one or more phospholipids. The one or more phospholipids may include, for example, phosphatidylcholine, phosphatidylglycerol, lecithin, β, γ-dipalmitoyl-α-lecithin, sphingomyelin, phosphatidylserine, phosphatidic acid, N-(2,3-di(9-(Z)-octadecenyloxy))-prop-1-yl-N,N,N-trimethylam monium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, 1,2-dipalmitoyl-sn-glycero-3-phosphothioethanol, and combinations thereof. In some cases, a shell (e.g., a bilayer) of a structure includes 50-200 natural or synthetic lipids or lipid analogs (e.g., phospholipids). For example, the shell may include less than about 500, less than about 400, less than about 300, less than about 200, or less than about 100 natural or synthetic lipids or lipid analogs (e.g., phospholipids), e.g., depending on the size of the structure.

Non-phosphorus containing lipids may also be used such as stearylamine, docecylamine, acetyl palmitate, and fatty acid amides. In other embodiments, other lipids such as fats, oils, waxes, cholesterol, sterols, fat-soluble vitamins (e.g., vitamins A, D, E and K), glycerides (e.g., monoglycerides, diglycerides, triglycerides) can be used to form portions of a structure described herein.

A portion of a structure described herein such as a shell or a surface of a nanostructure may optionally include one or more alkyl groups, e.g., an alkane-, alkene-, or alkyne-containing species, that optionally imparts hydrophobicity to the structure. An "alkyl" group refers to a saturated aliphatic group, including a straight-chain alkyl group, branched-chain alkyl group, cycloalkyl (alicyclic) group, alkyl substituted cycloalkyl group, and cycloalkyl substituted alkyl group. The alkyl group may have various carbon numbers, e.g., between $C_2$ and $C_{40}$, and in some embodiments may be greater than $C_5$, $C_{10}$, $C_{15}$, $C_{20}$, $C_{25}$, $C_{30}$, or $C_{35}$. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The alkyl group may include any suitable end group, e.g., a thiol group, an amino group (e.g., an unsubstituted or substituted amine), an amide group, an imine group, a carboxyl group, or a sulfate group, which may, for example, allow attachment of a ligand to a nanostructure core directly or via a linker. For example, where inert metals are used to form a nanostructure core, the alkyl species may include a thiol group to form a metal-thiol bond. In some instances, the alkyl species includes at least a second end group. For example, the species may be bound to a hydrophilic moiety such as polyethylene glycol. In other embodiments, the second end group may be a reactive group that can covalently attach to another functional group. In some instances, the second end group can participate in a ligand/receptor interaction (e.g., biotin/streptavidin).

In some embodiments, the shell includes a polymer. For example, an amphiphilic polymer may be used. The polymer may be a diblock copolymer, a triblock copolymer, etc., e.g., where one block is a hydrophobic polymer and another block is a hydrophilic polymer. For example, the polymer may be a copolymer of an α-hydroxy acid (e.g., lactic acid) and polyethylene glycol. In some cases, a shell includes a hydrophobic polymer, such as polymers that may include certain acrylics, amides and imides, carbonates, dienes, esters, ethers, fluorocarbons, olefins, sytrenes, vinyl acetals, vinyl and vinylidene chlorides, vinyl esters, vinyl ethers and ketones, and vinylpyridine and vinylpyrrolidones polymers. In other cases, a shell includes a hydrophilic polymer, such as polymers including certain acrylics, amines, ethers, styrenes, vinyl acids, and vinyl alcohols. The polymer may be charged or uncharged. As noted herein, the particular components of the shell can be chosen so as to impart certain functionality to the structures.

Where a shell includes an amphiphilic material, the material can be arranged in any suitable manner with respect to the nanostructure core and/or with each other. For instance, the amphiphilic material may include a hydrophilic group that points towards the core and a hydrophobic group that extends away from the core, or, the amphiphilic material may include a hydrophobic group that points towards the core and a hydrophilic group that extends away from the core. Bilayers of each configuration can also be formed.

The structures described herein may also include one or more proteins, polypeptides and/or peptides (e.g., synthetic peptides, amphiphilic peptides). In one set of embodiments, the structures include proteins, polypeptides and/or peptides that can increase the rate of cholesterol transfer or the cholesterol-carrying capacity of the structures. The one or more proteins or peptides may be associated with the core (e.g., a surface of the core or embedded in the core), the shell (e.g., an inner and/or outer surface of the shell, and/or embedded in the shell), or both. Associations may include covalent or non-covalent interactions (e.g., hydrophobic and/or hydrophilic interactions, electrostatic interactions, van der Waals interactions).

An example of a suitable protein that may associate with a structure described herein is an apolipoprotein, such as apolipoprotein A (e.g., apo A-I, apo A-II, apo A-IV, and apo A-V), apolipoprotein B (e.g., apo B48 and apo B100), apolipoprotein C (e.g., apo C-I, apo C-II, apo C-III, and apo C-IV), and apolipoproteins D, E, and H. Specifically, apo $A_1$, apo $A_2$, and apo E promote transfer of cholesterol and cholesteryl esters to the liver for metabolism and may be useful to include in structures described herein. Additionally or alternatively, a structure described herein may include one or more peptide analogues of an apolipoprotein, such as one described above. A structure may include any suitable number of, e.g., at least 1, 2, 3, 4, 5, 6, or 10, apolipoproteins or analogues thereof. In certain embodiments, a structure includes 1-6 apolipoproteins, similar to a naturally occurring HDL particle. Of course, other proteins (e.g., non-apolipoproteins) can also be included in structures described herein.

Optionally, one or more enzymes may also be associated with a structure described herein. For example, lecithin-cholesterol acyltransferase is an enzyme which converts free cholesterol into cholesteryl ester (a more hydrophobic form of cholesterol). In naturally-occurring lipoproteins (e.g., HDL and LDL), cholesteryl ester is sequestered into the core of the lipoprotein, and causes the lipoprotein to change from a disk shape to a spherical shape. Thus, structures described herein may include lecithin-cholesterol acyltransferase to mimic HDL and LDL structures. Other enzymes such as cholesteryl ester transfer protein (CETP) which transfers esterified cholesterol from HDL to LDL species may also be included.

In some cases, one or more bioactive agents are associated with a structure or a composition described herein. The one or more bioactive agents may optionally be released from the structure or composition (e.g., long-term or short-term release). Bioactive agents include molecules that affect a biological system and include, for example proteins, nucleic acids, therapeutic agents, vitamins and their derivatives, viral fractions, lipopolysaccharides, bacterial fractions and hormones. Other agents of interest may include chemotherapeutic agents, which are used in the treatment and management of cancer patients. Such molecules are generally characterized as antiproliferative agents, cytotoxic agents and immunosuppressive agents and include molecules such as taxol, doxorubicin, daunorubicin, vinca-alkaloids, actinomycin and etoposide.

Other examples of bioactive agents include cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories (e.g., glucocorticoids such as prednisone), nucleic acid species (e.g., anti-sense and siRNA species against inflammatory mediators), antineoplastics, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodilators, hypoglycemic agents, hypolipidemic agents, agents useful for erythropoiesis stimulation, antiulcer/antireflux agents, antinauseants/antiemetics and oil-soluble vitamins, cholesterol agents (e.g., statins such as Lipitor, Zocor, which may be known to lower cholesterol levels), or combinations thereof.

In some embodiments, one or more nucleic acids is associated with a structure described herein. A nucleic acids includes any double strand or single strand deoxyribonucleic acid (DNA) or ribonucleic acid (RNA) of variable length. Nucleic acids include sense and anti-sense strands. Nucleic acid analogs such as phosphorothioates, phosphoramidates, phosphonates analogs are also considered nucleic acids and may be used. Nucleic acids also include chromosomes and chromosomal fragments.

One or more sugar residues can optionally be associated with structures described herein.

In some embodiments, the articles and methods described herein can be used for targeting, such that the structures described herein can be delivered to specific target sites. Targeting may include functionalizing the structure with one or more ligands or receptors specific for a particular target site or sites. For instance, a structure described herein may include a ligand for a receptor (or a receptor for a ligand) that is expressed on the surface of a site to be targeted. For example, in certain embodiments, structures described herein include specific surface components that cause the structures to be retained in or aggregate at atherosclerotic plaques. The surface components specific for atherosclerotic plaques may depend on the particular stage of development of the plaque, as is known to those of ordinary skill in the art. Examples of specific surface components include antibodies (including antibody fragments and derivatives), plaque markers, specific cell surface markers, small molecules (e.g., folate), and aptamers, i.e., a nucleic acid able to specifically bind a specific target molecule, such as a biological moiety (e.g., RNA aptamers and DNA aptamers). Examples of specific targets in atherosclerotic plaques and in vascular endothelial cells in the vicinity of the plaque include but are not limited to: fibrin, macrophages, VCAM-1, E-selectin, integrin $[alpha]_v[beta]_3$, P-selectin and P-selectin glycoprotein ligand-1 (PSGL-1). Furthermore, a protein component of the structures described herein could be modified and used as the targeting molecule, e.g. Apo B, or Apo $A_1$. The structures may also include certain groups (e.g., asialo groups) for targeting specific small molecules.

It should be understood that the components described herein, such as the lipids, phospholipids, alkyl groups, polymers, proteins, polypeptides, peptides, enzymes, bioactive agents, nucleic acids, and species for targeting described above, may be associated with a structure in any suitable manner and with any suitable portion of the structure, e.g., the core, the shell, or both. For example, one or more such components may be associated with a surface of a core, an interior of a core, an inner surface of a shell, an outer surface of a shell, and/or embedded in a shell. Furthermore, such components can be used, in some embodiments, to facilitate the sequestration, exchange and/or transport of materials (e.g., proteins, peptides, polypeptides, nucleic acids, nutrients) from one or more components of a subject (e.g., cells, tissues, organs, particles, fluids (e.g., blood), and portions thereof) to a structure described herein, and/or from the structure to the one or more components of the subject. In some cases, the components have chemical and/or physical properties that allow favorable interaction (e.g., binding, adsorption, transport) with the one or more materials from the subject.

Additionally, the components described herein, such as the lipids, phospholipids, alkyl groups, polymers, proteins, polypeptides, peptides, enzymes, bioactive agents, nucleic acids, and species for targeting described above, may be associated with a structure described herein prior to administration to a subject or biological sample and/or after administration to a subject or biological sample. For example, in some cases a structure described herein includes a core and a shell which is administered in vivo or in vitro, and the structure has a greater therapeutic effect after sequestering one or more components (e.g., an apolipoprotein) from a subject or biological sample. That is, the structure may use natural components from the subject or biological sample to increase efficacy of the structure after it has been administered.

Figure 2A:
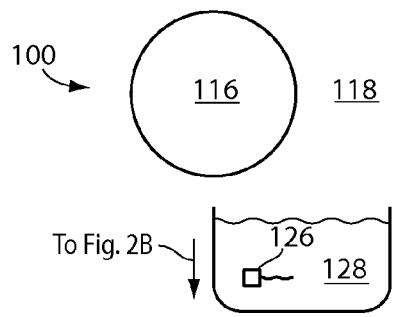
FIGS. 2A-2E show methods for fabricating various structures according to one set of embodiments.

In one aspect, methods of making structures described herein are provided. As shown in the embodiment illustrated in FIG. 2A, a method 100 includes providing a fluid comprising a plurality of nanostructures 116 (e.g., nanostructure cores) and a first solvent 118, as well as a fluid comprising a plurality of components 126 and a second solvent 128. First solvent 118 may be chosen such that it stabilizes nanostructures 116, preventing the nanostructures from precipitating out of solution. Second solvent 128 may be chosen so as to solubilize components 126. The first and second solvents may be miscible in some embodiments, and immiscible in other embodiments. In certain embodiments in which solvents 118 and 128 are miscible with one another, the solvents may also be miscible with water. Such and other solvents may be useful in a single-phase synthesis. Solvents that are miscible or slightly miscible with water are known to those or ordinary skill in the art and include, for example, alcohols (e.g., ethanol, propanol), THF, DMF and DMSO. Organic solvents that are immiscible with water can also be used (e.g., in two-phase synthesis).

Figure 2B:
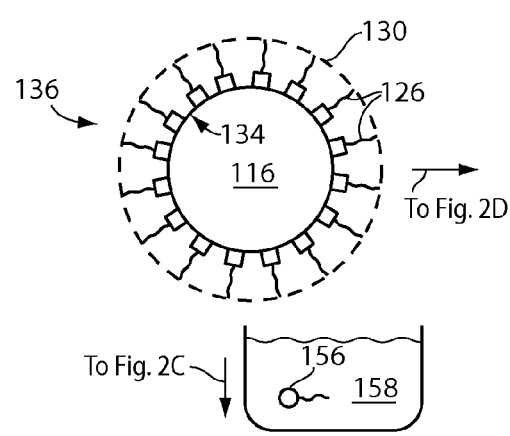

As shown in FIG. 2B, when components 126 are combined with nanostructures 116, a shell 130 comprising components 126 is formed on surface 134 of the nanostructure to form structure 136. As shown illustratively in FIG. 2B, the shell includes a monolayer of components 126, however, in other embodiments, multi-layers can be formed (e.g., at least two or at least three layers). If additional components are desired, the components can be combined with structure 136 and the components may associate with at least a portion of shell 130. For example, as shown in the embodiment illustrated in FIG. 2C, a second component 156 present in a third solvent 158 may be combined with nanostructure 136 to form a structure 152 including a shell 130 in the form of a bilayer. The bilayer may form due to favorable interaction between components 126 and 156, which may be the same or different. In certain embodiments, components 126 and 156 interdigitate.

Figure 2D:
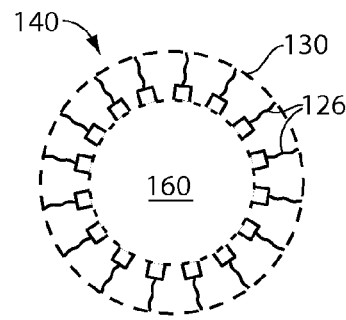
Figure 2C:
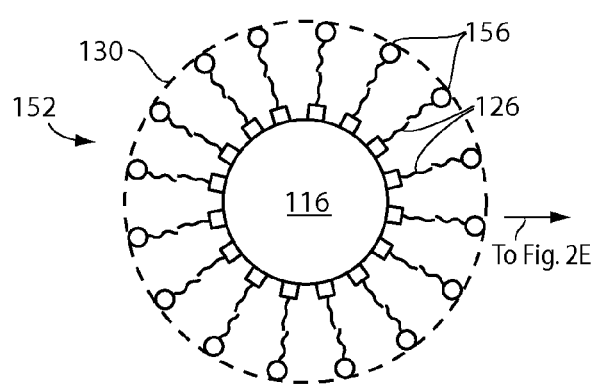

Optionally, all or a portion of nanostructure 116 may be removed from an assembled structure to form a partially or wholly hollow core. For example, as illustrated in FIG. 2D, structure 140 includes a shell 130 comprising a plurality of components 126 surrounding a hollow core 160. Nanostructure 116 can be removed from the structure by a variety of methods, which may depend on the particular material used to form nanostructure 116. For instance, where nanostructure 116 is a metal (e.g., gold) nanoparticle, solvents that are known to dissolve certain metals, such as iodine, potassium cyanide, and strong acids (e.g., nitric acid), can be used to remove the nanostructure core. Accordingly, in some cases where the core is formed of a metal (e.g., Au(0)), removal of the metal may include oxidizing the metal to form a metal salt, e.g., Au(0) to $Au^+$ and/or $Au^{3+}$. Electrochemical and redox methods can also be used to remove all or portions of a core. In some cases, a portion, but not all of the nanostructure core is removed, e.g., such that the nanostructure core is now more porous than before the removal step. In other cases, the core is released from the shell without removing a portion of the core. For example, a shell that is bonded to a metal core via sulfur-metal bonds can be released from the core by using small molecules such as dithiothreitol (DTT), which can displace the bonds. A suitable solvent or a chemical may be chosen such that it can remove at least portions of a core material, and/or release the shell from the core, without negatively affecting the shape and/or configuration of the shell, and/or degrade (e.g., denature) the components of the shell.

In certain embodiments, components 126 are cross linked with one another prior to removing all or a portion of the nanostructure core. For example, components 126 may be thiolated ligands which cross link by forming disulfide bonds. Any suitable method for cross linking can be used, such as photo cross linking, chemical cross linking, and oxidation-reduction methods, as known to those of ordinary skill in the art. The cross linking step may help to stabilize shell 130 in the same or a similar configuration as that achieved when associated with nanostructure 116. In certain embodiments, cross linking of components 126 is performed at the same time as the removal of nanostructure 116 to form a partially or wholly hollow structure.

Figure 2E:
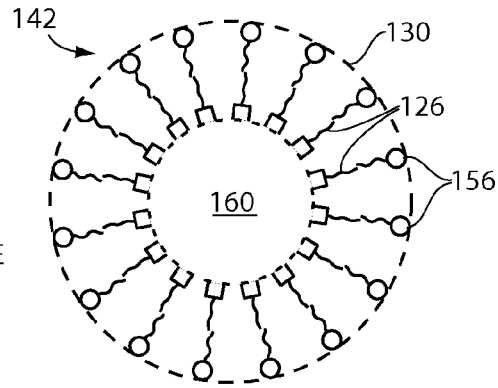

As illustrated in FIG. 2E, a similar approach for removing all or a portion of nanostructure 116 can be used to form structure 142, which includes a shell 130 comprising a bilayer of components 126 and 156, surrounding a hollow core 160.

In some cases, instead of forming multiple layers of components on a nanostructure surface in separate steps, multi-layers can be formed in a single step. For instance, components 126, components 156, and nanostructures 116 may be combined in a single phase of a liquid, e.g., a liquid that solubilizes and/or stabilizes the components and the nanostructures. Such a liquid may, in some cases, comprise water, or a solvent that is miscible with water. In some such embodiments, at least a first layer including components 126 and a second layer including components 156 are formed by self-assembly. The first and second layers in such a process may, in some instances, be formed substantially simultaneously. Additional layers can also be formed by such a process. Each of the layers can include a single component, or mixtures of components. To facilitate formation of the layers, a portion of the liquid may be removed from the mixture, e.g., by applying heat to evaporate a solvent having a low boiling point.

The ratio of components and nanostructures can be tailored depending on, for example, the type of components and nanostructures, the solvent(s) used, and the method of fabrication of the structures. For instance, to obtain solubility in aqueous solution, a suitable ratio can be chosen such that there is an ample amount of a component on the surface of the nanostructure so as to maintain water solubility. Thus, in certain instances, if the concentration of a component is too low, the structures will not be stable. Furthermore, if the ratio is too high with certain components, certain undesirable structures may be formed instead of stable monodisperse structures. Those of ordinary skill in the art can determine suitable ratios by simple experimentation in combination with the description provided herein.

Furthermore, although not shown in FIG. 2, additional components such as proteins, nucleic acids, polymers, bioactive agents (e.g., cholesterol lowering agents) or other structures can be associated with the structures shown in FIGS. 2A-2E at any step. For example, in some embodiments additional structures are added at the same time as addition of components 126 and/or 156, prior to the addition of components 126 and/or 156, or after the addition of components 126 and/or 156.

Advantageously, using the methods described herein, liposome-like structures having a hollow core (or at least a partially hollow core) can be formed in a size range that is unique to certain existing liposomes. For example, for many existing liposomes formed from a phospholipid bilayer and having a hollow core, the liposomes are large enough (e.g., typically greater than about 100 nm in diameter) such that the phospholipid bilayer is capable of being formed. As one attempts to make liposomes of smaller diameter, the packing of phospholipid moieties becomes limited sterically thus making it difficult or impossible to form bilayered liposomal structures with small radii of curvature (e.g., smaller than about 100 nm in diameter). Methods described herein, however, can be used to form structures of smaller diameter (e.g., structures having a largest cross-sectional dimension of less than about 100 nm, or less than or equal to about 50 nm), since the use of a nanostructure core as a template allows the arrangement of components in a shell that is dictated, at least in part, by the size and shape of the nanostructure core. Such methods can be used to make biologically relevant structures having a surface chemistry that mimics certain molecules such as HDL and LDL.

Additionally, because structures described herein can be formed by the use of nanostructures that serve as a template, and because certain nanostructures can be provided (e.g., made or purchased) having relatively high uniformity in size, shape, and mass, the structures described herein may also have relatively high uniformity in size, shape, and mass. That is, a mixture of relatively uniform structures can be formed, where the plurality of structures have a distribution of cross-sectional dimensions such that no more than about 20%, 15%, 10%, or 5% of the structures have a cross-sectional dimension greater than about 20%, 15%, 10%, or 5% of the average cross-sectional dimension. Structures having relatively high uniformity are useful in certain compositions and methods described herein.

Furthermore, the structures that are formed using methods described herein may disperse in a liquid, instead of forming aggregates. Dispersions of structures described herein are useful in certain compositions and methods described herein.

Those of ordinary skill in the art can choose an appropriate components (e.g., components 126 and 156), nanostructure cores, and solvents useful for the formation of structures described herein by, for example, knowing the particular components and nanostructure cores that would lead to favorable structures, the physical properties of the components, nanostructures and solvents, and/or by a simple screening test. One simple screening test may include adding components (and/or nanostructures) to a solvent and determining whether the component (or nanostructure) is soluble or stabilized in the solvent and/or reacts with or is negatively affected by the solvent. Other simple tests can be conducted by those of ordinary skill in the art.

In one set of embodiments, the structures, compositions and methods described herein are used to diagnose, prevent, treat or manage diseases or bodily conditions associated with abnormal lipid levels. For instance, high density lipoprotein is a dynamic serum nanostructure protective against the development of atherosclerosis and resultant illnesses such as heart disease and stroke. By administering certain compositions and methods described herein, such as those including structures that mimic naturally occurring HDL, circulating serum HDL levels (e.g., low HDL levels) may be increased. This can provide a promising therapeutic approach to, for example, preventing and potentially reversing atherosclerosis by augmenting reverse cholesterol transport. In other embodiments, compositions and methods described herein may be used to decrease LDL levels (e.g., decrease high LDL levels) or temporarily increase LDL levels, e.g., by using structure that mimics naturally occurring LDL. Furthermore, in certain embodiments, diagnosis, prevention, treatment or management of diseases or bodily conditions associated with abnormal lipid levels may involve using the structures, compositions and methods described herein to augment reverse cholesterol transport (e.g., directly or indirectly) by way of augmenting the flux of cholesterol through and out of the body. Other diseases or bodily conditions associated with abnormal lipid levels which could benefit from the structures and/or compositions described herein include, for example, atherosclerosis, phlebosclerosis or any venous condition in which deposits of plaques containing cholesterol or other material are formed within the intima or inner media of veins, acute coronary syndromes, angina including, stable angina, unstable angina, inflammation, sepsis, vascular inflammation, dermal inflammation, congestive heart failure, coronary heart disease (CHD), ventricular arrythmias, peripheral vascular disease, myocardial infarction, onset of fatal myocardial infarction, non-fatal myocardial infarction, ischemia, cardiovascular ischemia, transient ischemic attacks, ischemia unrelated to cardiovascular disease, ischemia-reperfusion injury, decreased need for revascularization, coagulation disorders, thrombocytopenia, deep vein thrombosis, pancreatitis, non-alcoholic steatohepatitis, diabetic neuropathy, retinopathy, painful diabetic neuropathy, claudication, psoriasis, critical limb ischemia, impotence, dyslipidemia, hyperlipidemia, hyperlipoproteinemia, hypoalphalipoproteinemia, hypertriglyceridemia, any stenotic condition leading to ischemic pathology, obesity, diabetes including both Type I and Type II, ichtyosis, stroke, vulnerable plaques, lower-limb ulceration, severe coronary ischemia, lymphomas, cataracts, endothelial dysfunction, xanthomas, end organ dysfunction, vascular disease, vascular disease that results from smoking and diabetes, carotid and coronary artery disease, regress and shrink established plaques, unstable plaques, vessel intima that is weak, unstable vessel intima, endothelial injury, endothelial damage as a result of surgical procedures, morbidity associated with vascular disease, ulcerations in the arterial lumen, restenosis as a result of balloon angioplasty, protein storage diseases (e.g., Alzheimer's disease, prion disease), diseases of hemostasis (e.g., thrombosis, thrombophilia, disseminated intravascular coagulation, thrombocytopenia, heparin induced thrombocytopenia, thrombotic thrombocytopenic purpura), rheumatic diseases (e.g., multiple sclerosis, systemic lupus erythematosis, sjogren's syndrome, polymyositis/dermatomyositis, scleroderma), neurological diseases (e.g., Parkinson's disease, Alzheimer's disease), and subindications thereof.

Structures, compositions, and methods described herein may diagnose, prevent, treat, or manage diseases or bodily conditions associated with abnormal lipid levels, by, for example, decreasing triglycerides levels, increasing or decreasing the level of other lipids, increasing plaque stability or decreasing the probability of plaque rupture, increasing or decreasing vasodilation, treating or preventing inflammation, treating or preventing inflammatory diseases or an inflammatory response, strengthening or stabilizing smooth muscle and vessel intima, stimulating efflux of extracellular cholesterol for transport to the liver, modulating immune responses, mobilizing cholesterol from atherosclerotic plaques, and modifying any membrane, cell, tissue, organ, and extracellular region and/or structure in which compositional and/or functional modifications would be advantageous.

In one particular embodiment, structures, compositions and methods described herein are used for treating atherosclerosis. Treating atherosclerosis may include performing a therapeutic intervention that results in reducing the cholesterol content of at least one atherosclerotic plaque, or prophylactically inhibiting or preventing the formation or expansion of an atherosclerotic plaque. Generally, the volume of the atherosclerotic plaque, and hence the degree of obstruction of the vascular lumen, will also be reduced. The present structures, compositions and methods are particularly useful for treating atherosclerotic lesions associated with familial hyperlipidemias.

The compositions and methods described herein may reduce the cholesterol content of atherosclerotic plaques and/or the volume of atherosclerotic plaques. The cholesterol content may be reduced by, for example, at least 10%-30%, at least 30%-50%, and in some instances at least 50%-85% or more. The volume of the atherosclerotic plaques may also be reduced. The reduction in plaque volume may be, for example, at least 5%-30%, often as much as 50%, and in some instances 75% or more. Methods of determining the reduction of cholesterol content of atherosclerotic plaques and/or the volume of atherosclerotic plaques are known to those of ordinary skill in the art, and include intravascular ultrasound and magnetic resonance imaging.

In another embodiment, structures, compositions and methods described herein are used for treating a subject having a vascular or a cardiovascular condition or is at risk of developing a cardiovascular condition are provided. Vascular conditions are conditions that involve the blood vessels (arteries and veins). Cardiovascular conditions are conditions that involve the heart and the blood vessels associated with the heart. Examples of vascular conditions include diabetic retinopathy, diabetic nephropathy, renal fibrosis, hypertension, atherosclerosis, arteriosclerosis, atherosclerotic plaque, atherosclerotic plaque rupture, cerebrovascular accident (stroke), transient ischemic attack (TIA), peripheral artery disease, arterial occlusive disease, vascular aneurysm, ischemia, ischemic ulcer, heart valve stenosis, heart valve regurgitation and intermittent claudication. Examples of cardiovascular conditions include coronary artery disease, ischemic cardiomyopathy, myocardial ischemia, and ischemic or post-myocardial ischemia revascularization.

Structures, compositions and methods described herein can also be used for treating a subject at risk for developing a cardiovascular condition. The degree of risk of a cardiovascular condition depends on the multitude and the severity or the magnitude of the risk factors that the subject has. Risk charts and prediction algorithms are available for assessing the risk of cardiovascular conditions in a human subject based on the presence and severity of risk factors. One commonly used algorithm for assessing the risk of a cardiovascular condition in a human subject based on the presence and severity of risk factors is the Framingham Heart Study risk prediction score. A human subject is at an elevated risk of having a cardiovascular condition if the subject's 10-year calculated Framingham Heart Study risk score is greater than 10%. Another method for assessing the risk of a cardiovascular event in a human subject is a global risk score that incorporates a measurement of a level of a marker of systemic inflammation, such as CRP, into the Framingham Heart Study risk prediction score. Other methods of assessing the risk of a cardiovascular event in a human subject include coronary calcium scanning, cardiac magnetic resonance imaging, and/or magnetic resonance angiography.

The structures, compositions and methods described herein may also be useful for prophylactic treatments. Prophylactic treatments may be useful following invasive vascular procedures. For instance, vascular regions having injured endothelium are at increased risk for developing atherosclerotic plaques. Therefore, invasive vascular procedures, such as coronary angioplasty, vascular bypass grafting, and other procedures that injure the vascular endothelial layer, may be practiced in conjunction with the methods of the present invention. As the invasive procedure injures the endothelium, the structures may act to remove cholesterol from the injured region and inhibit or prevent plaque formation of expansion during endothelial healing.

Hyperlipidemias may also be treated by the compositions and methods described herein. Administration of structures, alone or bound to a protein such as apo-A1 and apo-A2, to individuals having hypoalphalipoproteinemia from genetic or secondary causes, familial combined hyperlipidemia, and familial hypercholesterolemia is a useful treatment.

In certain embodiments, structures and compositions described herein are used in a method involving the determination of a disease or condition of a subject or biological sample. For instance, a method may include introducing a composition comprising a plurality of structures described herein to a subject or a biological sample (e.g., in vitro or in vivo), and exposing the plurality of nanostructures and/or the subject or biological sample to testing conditions that can determine a disease or condition of the subject or biological sample.

In some instances, the testing conditions are imaging conditions. The method may include, for example, administering a composition to a subject or biological sample by injection, infusion, or any other known method, optionally allowing the structures of the composition to accumulate in the subject or biological sample, and imaging the area of the subject or biological sample wherein the event of interest is located. Imaging conditions may include, for example, magnetic resonance imaging (MRI) conditions, X-ray conditions, ultrasound imaging conditions, and the use of radionuclides. The useful dosage to be administered and the particular mode of administration will vary depending upon such factors as age, weight, and particular region to be treated, as well as the particular composition used, the diagnostic use contemplated, and the form of the formulation, for example, suspension, emulsion, or the like, as will be readily apparent to those skilled in the art.

It should be understood that any suitable structures described herein can be used in such methods, including, for example, structures having a nanostructure core comprising an inorganic material and a shell substantially surrounding and attached to the nanostructure core. In some cases, such structures are adapted to sequester cholesterol. In other cases, the structures are a marker for a disease or bodily condition.

In some embodiments, the structures can be imaged in localized regions within a blood vessel. For instance, the structures may be localized in a blood vessel having a high concentration of cholesterol, e.g., in the form of plaque, and imaging of the vessel can result in the determination of the location of the plaque. Without wishing to be bound by theory, it is believed that the structures localize in a blood vessel due to, at least in part, turbulent flow in the blood vessel. It has long been appreciated that plaques develop at arterial branch points (e.g., coronary arteries, carotid, iliac vessels in legs, femoral vessels), which are natural sites of turbulence. At such sites, eddy currents develop where arterial flow near the vessel wall at the site of turbulence slows down and at times even reverses flow. This is thought to marginate small particles (including the structures described herein), which can then interact with and move through the endothelium and into the lamina propria at these sites due to their small size, and set up the inflammatory reaction and cholesterol deposition events that lead to vessel remodeling and plaque formation. Accordingly, in some cases, the structures described herein may cross the endothelium of the blood vessel, thus becoming localized in the general vicinity of the turbulent flow region. In certain embodiments, the structures may be endocytosed by a cell, thereby becoming localized within the cell.

In some cases, the structures may be used as contrast agents. For example, the nanostructure core of the structure may comprise a material suitable for use as a contrast agent (e.g., gold, iron oxide, a quantum dot, radionuclide, etc.). In other embodiments, the shell may include a contrast agent. For instance, a nanoparticle or other suitable contrast agent may be embedded within the lipid bilayer of the shell, or associated with an inner or outer surface of the shell. The contrast agents may be used to enhance various imaging methods known to those in the art such as MRI, X-ray, PET, CT, etc.

In other embodiments, a composition is introduced to a subject or a biological sample, and the structures of the composition and/or the subject or biological sample are exposed to assay conditions that can determine a disease or condition of the subject or biological sample. At least a portion of the structures may be retrieved from the subject or biological sample and an assay may be performed with the structures retrieved. The structures may be assayed for the amount and/or type of molecules bound to or otherwise sequestered by the structures. For example, in one set of embodiments, a competition assay is performed, e.g., where labeled cholesterol is added and displacement of cholesterol is monitored. The more measured uptake of labeled cholesterol, the less bound un-labeled free cholesterol is present. This can be done, for example, after a composition comprising the structures described herein are administered to a subject or a biological sample, and the structures are subsequently retrieved from the subject or biological sample. This method can be used, for example, where the structures are to be used as a diagnostic agent to see how much cholesterol (unlabeled) it has sequestered in a subject or biological sample.

Other methods can also be used to determine the amount of cholesterol sequestered by structures described herein. In some cases, labeled cholesterol (e.g., fluorescently-labeled cholesterol such as NBD-cholesterol, or radioactive cholesterol) can be used. Labeled cholesterol can be added to the structures either in vitro or in vitro. By adding structures without labeled cholesterol and measuring the fluorescence increase upon binding, one can calculate the binding constant of labeled cholesterol to the structure. In addition, to remove the cholesterol from the structure, one can dissolve the particle (e.g., KCN) and then measure the resultant fluorescence in solution. Comparing to standard curve can allow determination of the number of cholesterol molecules per particle. Other methods such as organic extraction and quantitative mass spectrometry can also be used to calculate amount of cholesterol sequestered by one or more structures described herein.

As described herein, the inventive structures may be used in "pharmaceutical compositions" or "pharmaceutically acceptable" compositions, which comprise a therapeutically effective amount of one or more of the structures described herein, formulated together with one or more pharmaceutically acceptable carriers, additives, and/or diluents. The pharmaceutical compositions described herein may be useful for diagnosing, preventing, treating or managing a disease or bodily condition such as those described herein, including but not limited to ones associated with abnormal lipid levels. It should be understood that any suitable structures described herein can be used in such pharmaceutical compositions, including those described in connection with the figures. In some cases, the structures in a pharmaceutical composition have a nanostructure core comprising an inorganic material and a shell substantially surrounding and attached to the nanostructure core. The structures may be adapted to sequester cholesterol, and in certain instances, are a marker for a disease or bodily condition.

The pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The structures described herein may be orally administered, parenterally administered, subcutaneously administered, and/or intravenously administered. In certain embodiments, a structure or pharmaceutical preparation is administered orally. In other embodiments, the structure or pharmaceutical preparation is administered intravenously. Alternative routes of administration include sublingual, intramuscular, and transdermal administrations.

Pharmaceutical compositions described herein include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

The inventive compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a structure described herein as an active ingredient. An inventive structure may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered structure is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the structures described herein include pharmaceutically acceptable emulsions, microemulsions, solutions, dispersions, suspensions, syrups and elixirs. In addition to the inventive structures, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions described herein (e.g., for rectal or vaginal administration) may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the body and release the structures.

Dosage forms for the topical or transdermal administration of a structure described herein include powders, sprays, ointments, pastes, foams, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to the inventive structures, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the structures described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a structure described herein to the body. Dissolving or dispersing the structure in the proper medium can make such dosage forms. Absorption enhancers can also be used to increase the flux of the structure across the skin. Either providing a rate controlling membrane or dispersing the structure in a polymer matrix or gel can control the rate of such flux.

Ophthalmic formulations, eye ointments, powders, solutions and the like, are also contemplated as being within the scope of this invention.

Pharmaceutical compositions described herein suitable for parenteral administration comprise one or more inventive structures in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the inventive structures may be facilitated by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with structures and compositions described herein include time-release, delayed release, sustained release, or controlled release delivery systems, as described herein. Such systems may avoid repeated administrations of the structures in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The compositions may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiments. The structures and compositions described herein can also be combined (e.g., contained) with delivery devices such as syringes, pads, patches, tubes, films, MEMS-based devices, and implantable devices.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

Injectable depot forms can be made by forming microencapsule matrices of the structures described herein in biodegradable polymers such as polylactide-polyglycolide. Depending on the ratio of structure to polymer, and the nature of the particular polymer employed, the rate of release of the structure can be controlled. Examples of other biodegradable polymers include poly(orthoesters) and poly(anhydrides).

When the structures described herein are administered as pharmaceuticals, to humans and animals, they can be given per se or as a pharmaceutical composition containing, for example, about 0.1% to about 99.5%, about 0.5% to about 90%, or the like, of structures in combination with a pharmaceutically acceptable carrier.

The administration may be localized (e.g., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the structures described herein, which may be used in a suitable hydrated form, and/or the inventive pharmaceutical compositions, are formulated into pharmaceutically-acceptable dosage forms by conventional methods known to those of skill in the art.

The compositions described herein may be given in dosages, e.g., at the maximum amount while avoiding or minimizing any potentially detrimental side effects. The compositions can be administered in effective amounts, alone or in a combinations with other compounds. For example, when treating cancer, a composition may include the structures described herein and a cocktail of other compounds that can be used to treat cancer. When treating conditions associated with abnormal lipid levels, a composition may include the structures described herein and other compounds that can be used to reduce lipid levels (e.g., cholesterol lowering agents).

The phrase "therapeutically effective amount" as used herein means that amount of a material or composition comprising an inventive structure which is effective for producing some desired therapeutic effect in a subject at a reasonable benefit/risk ratio applicable to any medical treatment. Accordingly, a therapeutically effective amount may, for example, prevent, minimize, or reverse disease progression associated with a disease or bodily condition. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more structures described herein may be from about 10 ng/kg of body weight to about 1000 mg/kg of body weight, and the frequency of administration may range from once a day to once a month. However, other dosage amounts and frequencies also may be used as the invention is not limited in this respect. A subject may be administered one or more structure described herein in an amount effective to treat one or more diseases or bodily conditions described herein.

An effective amount may depend on the particular condition to be treated. One of ordinary skill in the art can determine what an effective amount of the composition is by, for example, methods such as assessing liver function tests (e.g. transaminases), kidney function tests (e.g. creatinine), heart function tests (e.g. troponin, CRP), immune function tests (e.g. cytokines like IL-1 and TNF-alpha), etc. The effective amounts will depend, of course, on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular inventive structure employed, the route of administration, the time of administration, the rate of excretion or metabolism of the particular structure being employed, the duration of the treatment, other drugs, compounds and/or materials used in combination with the particular structure employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the structures described herein employed in the pharmaceutical composition at levels lower than that required to achieve the desired therapeutic effect and then gradually increasing the dosage until the desired effect is achieved.

In some embodiments, a structure or pharmaceutical composition described herein is provided to a subject chronically. Chronic treatments include any form of repeated administration for an extended period of time, such as repeated administrations for one or more months, between a month and a year, one or more years, or longer. In many embodiments, a chronic treatment involves administering a structure or pharmaceutical composition repeatedly over the life of the subject. For example, chronic treatments may involve regular administrations, for example one or more times a day, one or more times a week, or one or more times a month. In general, a suitable dose such as a daily dose of a structure described herein will be that amount of the structure that is the lowest dose effective to produce a therapeutic effect. Such an effective dose will generally depend upon the factors described above. Generally doses of the structures described herein for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms. For example, instructions and methods may include dosing regimens wherein specific doses of compositions, especially those including structures described herein having a particular size range, are administered at specific time intervals and specific doses to achieve reduction of cholesterol (or other lipids) and/or treatment of disease while reducing or avoiding adverse effects or unwanted effects. Thus, methods of administering structures described herein, methods of reducing total and LDL cholesterol by the administration of the structures, methods of raising the level or increasing the efficacy of HDL cholesterol by the administration of structures described herein, and methods of dosing structures in patients in need thereof are described.

While it is possible for a structure described herein to be administered alone, it may be administered as a pharmaceutical composition as described above. The present invention also provides any of the above-mentioned compositions useful for diagnosing, preventing, treating, or managing a disease or bodily condition packaged in kits, optionally including instructions for use of the composition. That is, the kit can include a description of use of the composition for participation in any disease or bodily condition, including those associated with abnormal lipid levels. The kits can further include a description of use of the compositions as discussed herein. The kit also can include instructions for use of a combination of two or more compositions described herein. Instructions also may be provided for administering the composition by any suitable technique, such as orally, intravenously, or via another known route of drug delivery.

The kits described herein may also contain one or more containers, which can contain components such as the structures, signaling entities, and/or biomolecules as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are used, the liquid form may be concentrated or ready to use. The solvent will depend on the particular inventive structure and the mode of use or administration. Suitable solvents for compositions are well known and are available in the literature.

The kit, in one set of embodiments, may comprise one or more containers such as vials, tubes, and the like, each of the containers comprising one of the separate elements to be used in the method. For example, one of the containers may comprise a positive control in the assay. Additionally, the kit may include containers for other components, for example, buffers useful in the assay.

As used herein, a "subject" or a "patient" refers to any mammal (e.g., a human), for example, a mammal that may be susceptible to a disease or bodily condition such as a disease or bodily condition associated with abnormal lipid levels. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A subject may be a subject diagnosed with a certain disease or bodily condition or otherwise known to have a disease or bodily condition. In some embodiments, a subject may be diagnosed as, or known to be, at risk of developing a disease or bodily condition. In some embodiments, a subject may be diagnosed with, or otherwise known to have, a disease or bodily condition associated with abnormal lipid levels, as described herein. In certain embodiments, a subject may be selected for treatment on the basis of a known disease or bodily condition in the subject. In some embodiments, a subject may be selected for treatment on the basis of a suspected disease or bodily condition in the subject. In some embodiments, the composition may be administered to prevent the development of a disease or bodily condition. However, in some embodiments, the presence of an existing disease or bodily condition may be suspected, but not yet identified, and a composition of the invention may be administered to diagnose or prevent further development of the disease or bodily condition.

A "biological sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

The following examples are intended to illustrate certain embodiments of the present invention, but are not to be construed as limiting and do not exemplify the full scope of the invention.

EXAMPLE 1

This example demonstrates the formation of self-assembled lipid layers on gold nanoparticles and further demonstrates surface functionalization of the resulting structures with proteins.

Gold nanoparticles (AuNPs) were modified with several different attachment methodologies. Citrate-stabilized gold colloids having diameters (sizes) of 5 nm, 7 nm, 10 nm, 13 nm, and 30 nm were used as scaffolds to form lipid-functionalized AuNPs. All AuNPs were purchased from Ted Pella, Inc. and all lipids were purchased from Avanti Polar Lipids, Inc.

Figure 3A:
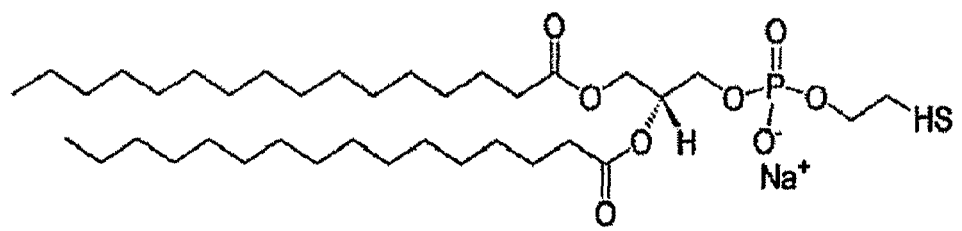
FIGS. 3A and 3B show the chemical structures of certain phospholipids that can be used to form a shell of a structure according to one set of embodiments.
Figure 3B:
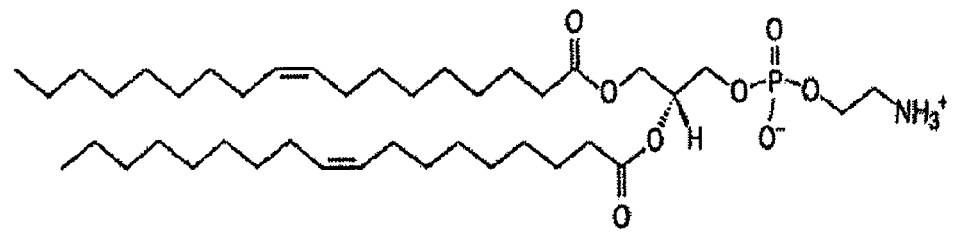

First, equal w/v solutions of 1,2-dipalmitoyl-sn-glycero-3-phosphothioethanol (SH-lipid, FIG. 3A) and L-alpha phosphatidylethanolamine or L-alpha phosphatidylcholine (N+-lipid, FIG. 3B) were prepared in a 1:1 solution of chloroform and ethanol in a final volume of 1 mL. The solvent was evaporated leaving behind the mixed lipids in powder form. The lipid mixture was re-suspended in 1 mL of gold nanoparticle colloid (e.g., 5 nm or 13 nm) in water, vortexed thoroughly and sonicated for 2 min.

Apolipoprotein A-I (Apo-AI) containing structures were prepared by adding 10 microliters of 100 ng/mL of the purified protein (Abcam, Inc., or Biodesign, Inc.) in water per 990 microliters of AuNPs (5 nm or 13 nm) in water prior to adding to the dry lipid mixture. Alternatively, the solution containing SH-lipid and N+-lipid can be prepared in a 1:1 solution of chloroform to ethanol, evaporated, and re-suspended in an equal volume of a 1 ng/mL solution of Apo-AI protein in water. The sample was vortexed thoroughly and sonicated for several minutes. The solvent was again evaporated and the lipid-apo mixture was resuspended in an equal volume of AuNPs in water, followed by thorough vortexing and sonication for 2 min.

Purification of lipid-functionalized AuNPs was accomplished via simple centrifugation (RPM depends upon the gold nanoparticle core used to template the LP structure). The structures were washed three times by removing the supernatant and re-suspending in water and finally resuspended in water, a buffered salt solution, or a buffered salt solution containing albumin.

In another formulation, 5 nm gold particles were surface functionalized with long chain thiolated alkane species in a first step (e.g., dodecanethiol) such that the N+ phospholipid was then added to the surface of the nanoparticle. The long chain alkane tails of the N+-phospholipid interdigitate in the species present on the surface of the particle and form stable water soluble structures accordingly. In a concomitant or separate step, Apo-AI was added to the surface of the structure.

Resultant structures have been characterized by a number of methodologies including MALDI TOF MS, dynamic light scattering (DLS), zeta potential measurement, electron microscopy, lipid fluorescence, and FT-IR. Data from the DLS and zeta potential experiments are shown in Tables 1 and 2, respectively.

TABLE 1

| Dynamic light scattering measurements | | |
|---|---|---|
| Sample | Average Diameter (nm) | Difference from Au NP (nm) |
| Au | 7.0 | — |
| Au + APO | 7.5 | +0.5 |
| APO1-di(3) | 12.2 | +5.2 |
| APO2-di(3) | 11.6 | +4.6 |
| Di(3) | 9.2 | +2.2 |
| Fluor-di(3) NAP filtered 1X | 14.0 | +7.1 |
| Fluor-di(3) NAP filtered 2X | 15.1 | +8.1 |

In Table 1, the DLS data are for lipid functionalized 5 nm AuNPs. Au represents a 5 nm gold colloid. Au+APO is gold colloid with surface adsorbed apolipoprotein A-I alone. APOI and 2-di(3) are 5 nm gold particles surface functionalized with both lipids and apolipoprotein A-I. Di(3) represents 5 nm gold particles with just the phospholipid bilayer (no apolipoprotein A-I), and Fluor-di(3)NAP filtered represents 5 nm particles surface functionalized with the thiolated lipid but with a fluorescently labeled phospholipid in the outer leaflet.

Table 4 depicts zeta potential measurements for 5 nm particles, which shows that the structures may include a surface charge. The labeling scheme is the same as that in Table 2.

TABLE 2

Zeta potential measurements

| Sample | Average Zeta Potential (mV) | Difference (mV) |
| --- | --- | --- |
| Au | −35.88 | 0 |
| Au + APO | −79.84 | −43.94 |
| APO1-di(3) | −37.22 | −1.32 |
| APO2-di(3) | −47.12 | −11.22 |
| Di(3) | −33.96 | +1.94 |
| Fluor-di(3) NAP filtered 1X | −10.14 | +25.76 |
| Fluor-di(3) NAP filtered 2X | −33.62 | +2.28 |

EXAMPLE 2

This example demonstrates the synthesis and characterization of high density lipoprotein (HDL) bio-mimetic structures capable of binding cholesterol.

Figure 4:
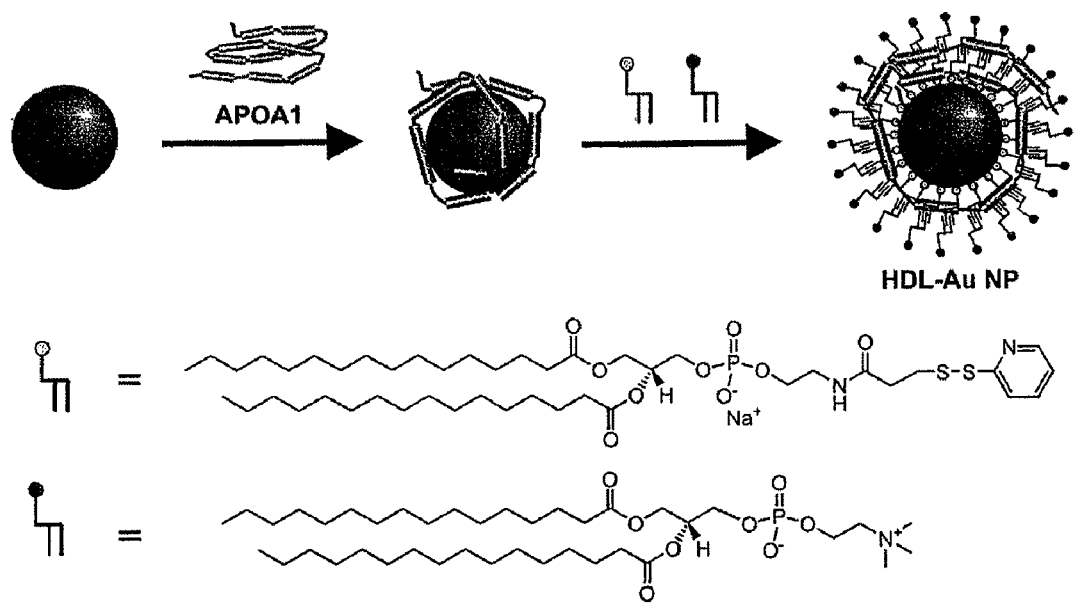
FIG. 4. shows a synthetic method for forming a co-self-assembled protein (APO-AI) lipid bilayer on a nanostructure core, according to one set of embodiments.

An aqueous suspension of citrate-stabilized gold nanoparticles (5±0.75 nm, 80 nM, Ted Pella, Inc.) was mixed with a 5-fold excess of purified Apo-AI (400 nM, Biodesign International) and stirred overnight at room temperature. Subsequently, a 1:1 solution of disulfide-functionalized lipid, 1,2-dipalmitoyl-sn-glycero-3-phosphoethanolamine-N-[3-(2-pyridyldithio)propionate] and amine-functionalized lipid, 1-2-dipalmitoyl-sn-glycero-3-phosphocholine (Avanti Polar Lipids) was mixed in $CHCl_3$ and added to the aqueous suspension of particles in 100-fold excess with respect to the Au NPs (FIG. 4). The disulfide lipid was selected since the disulfide functionality allows for chemisorption to the surface of the Au NP. The amine-modified lipid is a naturally occurring phospholipid known to electrostatically and hydrophobically associate with Apo A-1. This addition results in a two phase mixture. The mixture was vortexed and heated gradually to 65° C. in order to evaporate the $CHCl_3$. After allowing the solution to cool, purification of the HDL-Au NP structures was accomplished via repeated (2×) centrifugation (21,000 g) and re-suspension in Nanopure™ water or phosphate buffered saline with 0.05% (w/v) bovine serum albumin (PBS, 137 nM NaCl, 10 mM phosphate, 2.7 nM KCl, pH 7.4, Hyclone). If the disulfide lipid is added alone and without prior addition of Apo A-1, the structures precipitate since they become hydrophobic upon lipid adsorption to the Au NP surface.

Figure 5:
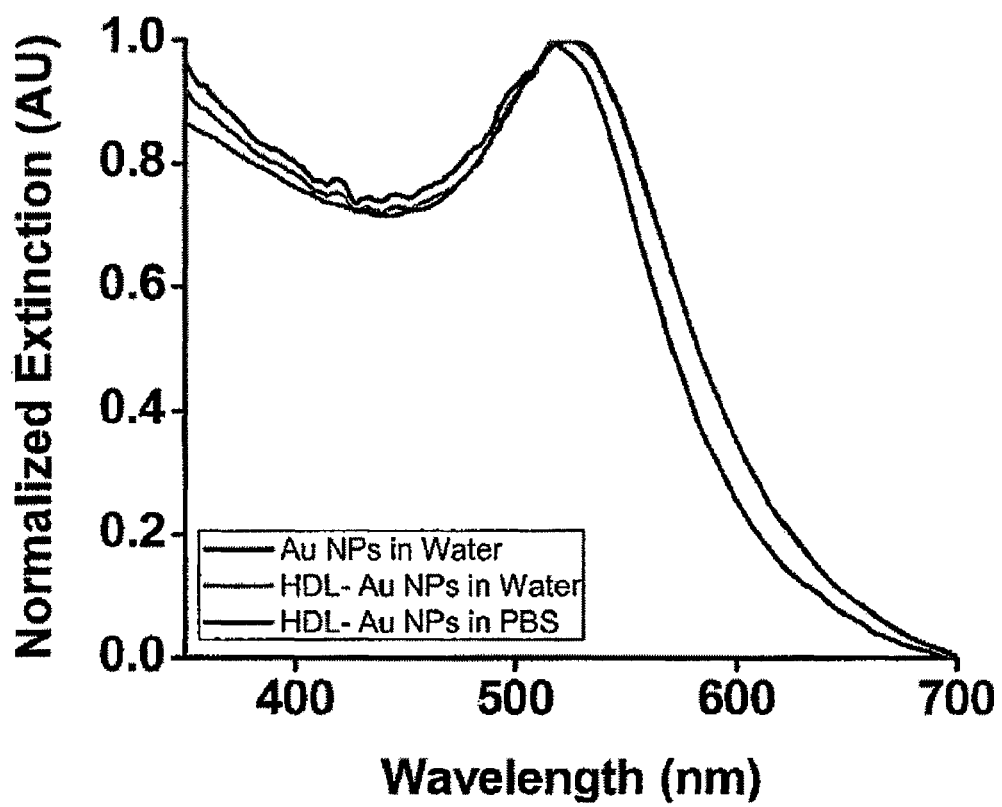
FIG. 5 shows UV-vis spectra of conjugated and unconjugated gold nanoparticles, according to one set of embodiments.

UV-Vis analysis of the purified HDL-Au NP structures exhibits a band at 520 nm (FIG. 5), consistent with dispersed rather than aggregated HDL-Au NP structures. Dynamic light scattering experiments were performed using a Zetasizer Nano ZS (Malvern) and were used to follow the Au NP surface modification process. The results demonstrated sequential growth of the HDL structures, as shown in Table 3. Unmodified gold colloid, (9.2 nm average hydrodynamic diameter) was first modified with Apo A-1 (11.0 nm) and then with the mixture of lipids (17.9 nm). The average size of the resulting HDL-AuNP structures was similar to that for natural HDL.

TABLE 3

Hydrodynamic diameters for conjugated and unconjugated gold nanoparticles

| Particles | Hydrodynamic Diameter (nm) |
| --- | --- |
| Au NP (5 nm diameter) | 9.2 ± 2.1 |
| Au NP + APOA1 | 11.0 ± 2.5 |
| Au NP + APOA1 + Phospholipids | 17.9 ± 3.1 |

In order to characterize the chemical composition of the HDL-Au NP structures, fluorophore labeled components (Apo A-1 and aminated phospholipids) were used to synthesize the HDL-Au NP structures. To measure the protein loading on the Au NPs, APOAI was fluorescently labeled using an Alexa Fluor 488 protein labeling kit (Invitrogen). HDL-Au NPs were synthesized using the procedure described above, and their concentration was determined by UV-Vis ($\epsilon$=1.2× $10^7$ L/mol cm). Gold nanoparticles were oxidized with KCN in order to liberate fluorescently bound Apo-AI, and the fluorescence of the solution was measured. The number of proteins per structure was determined by comparing the obtained fluorescence measurements to that of a standard curve prepared with known concentrations of labeled Apo-AI. Phospholipid loading on the HDL-Au NP structures was determined with similar experiments. The fluorescently modified phospholipid 1-palmitoyl-2 {6-[(7-nitro-2-1,3-benzoxadiazol-4-yl)amino]hexanoyl}-sn-glycero-phosphoethanolamine (Avanti Polar Lipids) was used in place of the aminated lipid to determine aminated lipid loading. The average number of proteins and aminated phospholipids per structure was determined to be 3±1 and 83±12, respectively. Thus, these values corresponded well to those reported for natural HDL.

Figure 6:
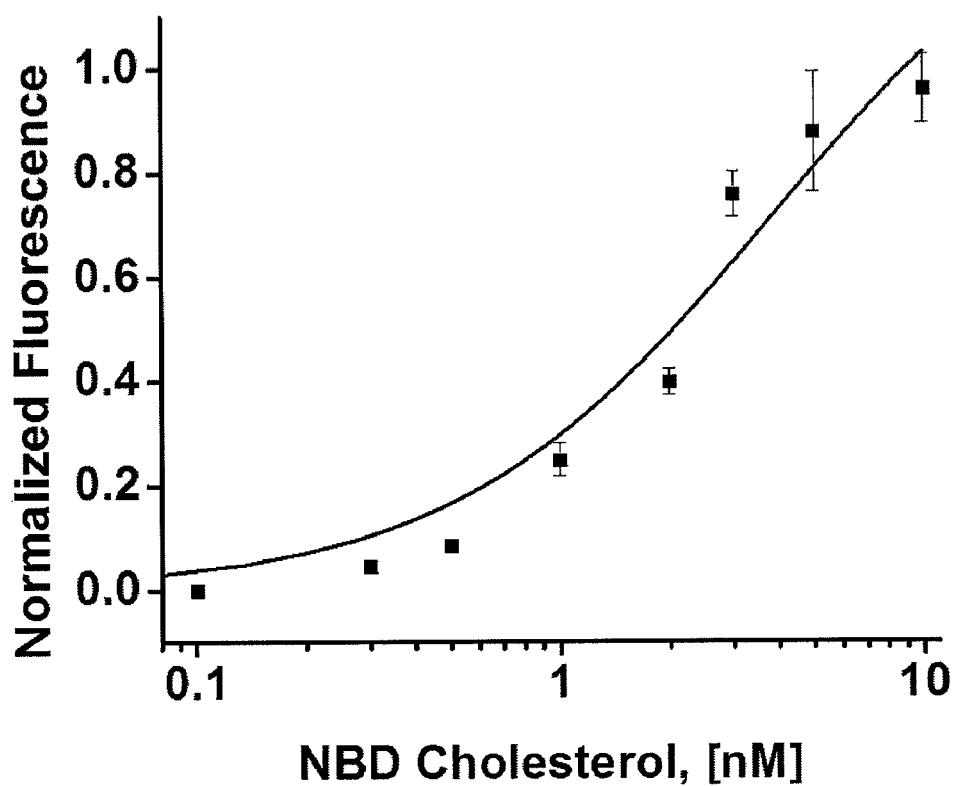
FIG. 6 shows a binding isotherm of NBD-cholesterol to structures described herein, according to one set of embodiments.

Transport of cholesterol to the liver by HDL is one mechanism by which HDL protects against the development of atherosclerosis. Thus, determining if HDL-AuNP structures bind cholesterol was important for determining the potential of these structures as therapeutic agents. The binding of cholesterol to HDL-Au NP structures was investigated with a fluorescent cholesterol analogue (25-{N-[(7-nitrobenz-2-oxa-1,3-diazol-4-yl)-methyl]amino}-27-norcholesterol, NBD-cholesterol). NBD-cholesterol fluorescence was weak in polar environments such as water; however, in non-polar matrices (such as a lipid membrane) NBD-cholesterol became fluorescent. Cholesterol binding to HDL-Au NP structures was determined by adding 5 microliters of varying concentrations of 25-{N-[(7-nitrobenz-2-oxa-1,3-diazol-4-yl)methyl]amino}-27-norcholesterol (NBD-cholesterol) in DMF to 995 microliters of 5 nM HDL-Au NPs in water. The solutions were vortexed and incubated for at least 20 min. Fluorescence spectra of the solutions were measured on a Jobin Yvon Fluorolog 3, and the solutions were excited at 473 nm and scanned from 500 to 600 nm in 1 nm increments with 1 sec integration times. The binding of NBD-cholesterol to HDL-Au NP structures lead to an increase in fluorescence intensity. The fluorescence intensity of control solutions of NBD-cholesterol without the HDL-Au NP structures were measured in order to subtract background signal from the samples. The fluorescence intensity increase at 520 nm upon NBD-cholesterol binding was used to construct a binding isotherm. The $K_d$ was determined by analyzing the binding curves with the "one site total binding" function in GraphPad Prism 5.0 software using the equation: Fluorescence=($B_{max}$*[NBD-cholesterol])/($K_d$+[NBD-cholesterol]). Quenching by the Au NP caused the signal of the HDL-Au NP bound NBD-cholesterol to be partially dampened. However, titration of NBD-cholesterol into a solution of HDL-Au NPs provided a strong enough fluorescent signal to construct a binding isotherm (FIG. 6). This isotherm was used to calculate a $K_d$ of ~4 nM for NBD-cholesterol binding to HDL-Au NP structures.

EXAMPLE 3

This example demonstrates the synthesis of stable structures including a gold nanoparticle core and a shell comprising self-assembled $C_{10}$ or $C_{15}$ lipids on the gold nanoparticle surface. This example demonstrates further surface functionalization of the structures with proteins.

Figure 7:
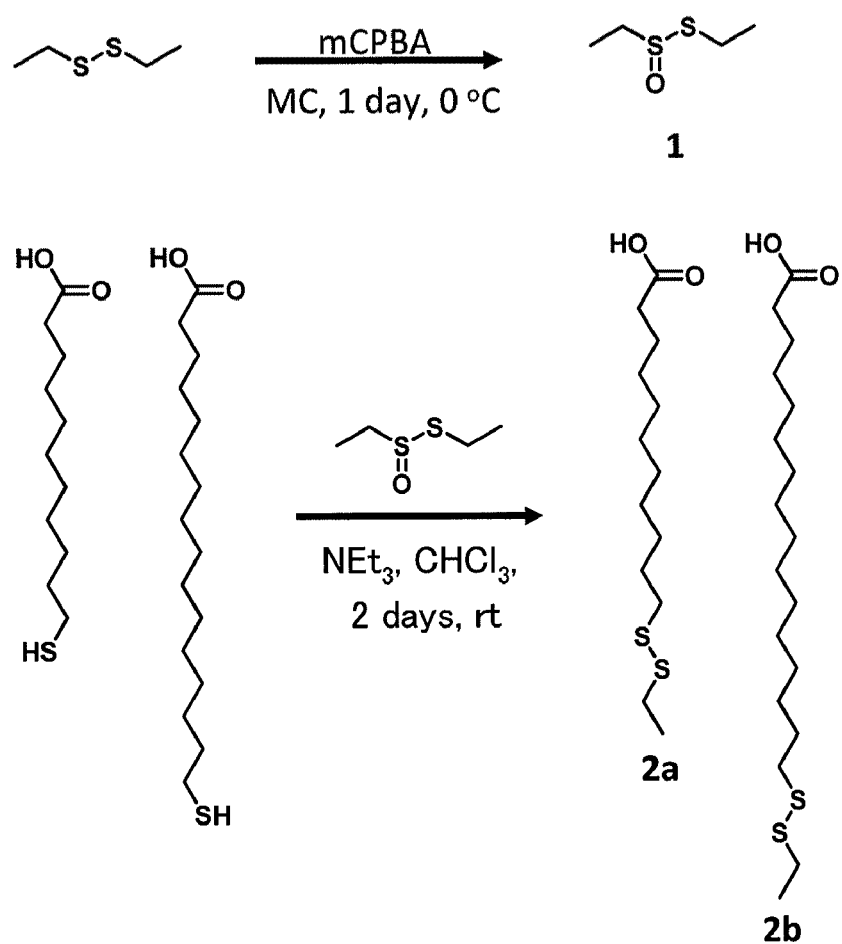
FIG. 7 shows the first steps of a synthetic route to compounds 3a,b and 4a,b shown in FIG. 8, according to one set of embodiments.
Figure 8:
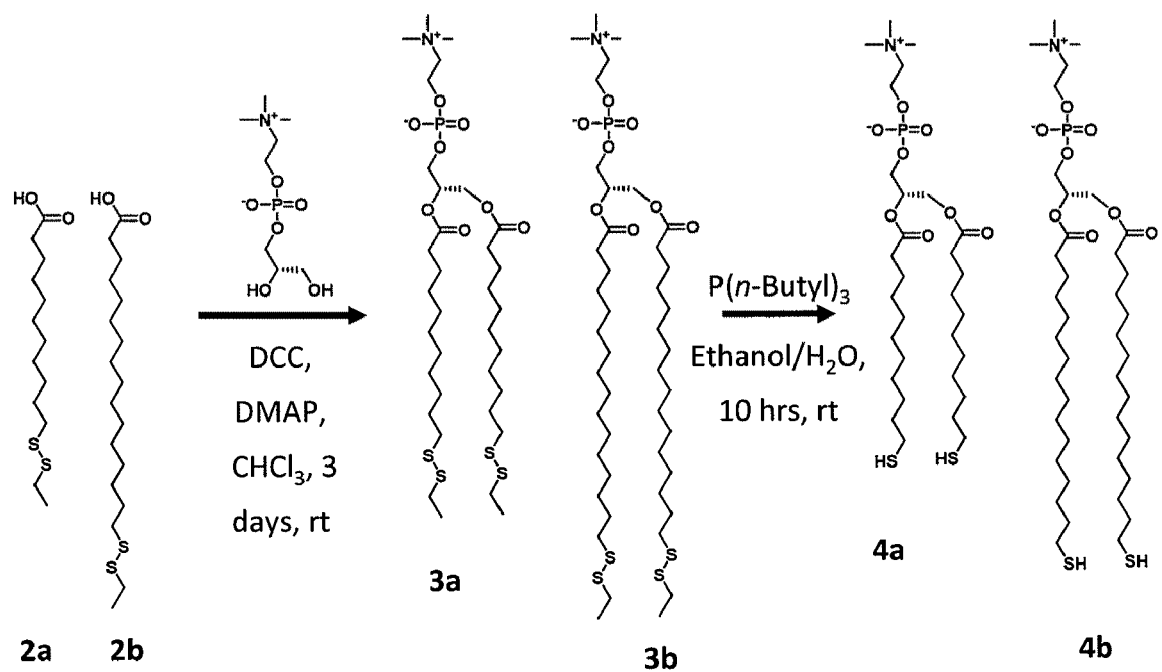
FIG. 8 shows various compounds that were used in the formation of structures described herein, according to one set of embodiments.

The scheme shown in FIG. 7 was used to synthesize $C_{10}$ and $C_{15}$ dithiol functionalized phospholipids, lipids 2a and 2b, using procedures described in Samuel et al., "Polymerized-depolymerized vesicles. Reversible thiol-disulfide-based phosphatidylcholine membranes," JACS, 107(1), 42-47 (1985), which is incorporated herein by reference in its entirety. The scheme in FIG. 8 was used to synthesize the compounds 3a, 3b, 4a, and 4b, also using procedures described in Samuel et al. In order to functionalize 5 nm gold nanoparticles (Au NPs) with either $C_{10}$ or $C_{15}$ lipids, the lipids were first dissolved in a 1:1 mix of ethanol and water (100 µM lipid). 160 microliters of this solution was syringe filtered (0.2 nm) into a glass vial and the and the solvent was removed using a rotary solvent evaporator. Two mL of 0.2 nm filtered 5 nm Au NPs (80 nM) was then added to the dried lipids. This solution was vortexed and allowed to incubate on a flat-top shaker for 12 hours. This solution was then sonicated hourly×3 hours, for approximately 1 minute. The solution was then transferred from the glass vial to an Eppendorf tube and centrifuged at 15K RPM for 40 minutes to pellet the $C_{10}$ or $C_{15}$ Au NP conjugates and to remove excess $C_{10}$ or $C_{15}$ lipids. Following centrifugation the supernatant was removed, and the $C_{10}$ or $C_{15}$ Au NP pellet was re-suspended in 1 mL water followed by vortex and sonication. The centrifugation procedure was repeated for further purification. For particle concentration, the supernatant was removed following centrifugation and the particles re-suspended (water or phosphate buffered saline) in smaller volume.

Figure 9A:
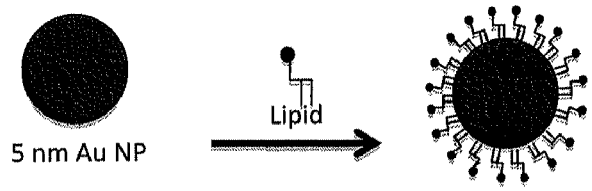
FIG. 9A shows a schematic diagram of a process for forming gold nanoparticles functionalized with lipids, according to one set of embodiments.
Figure 9A:
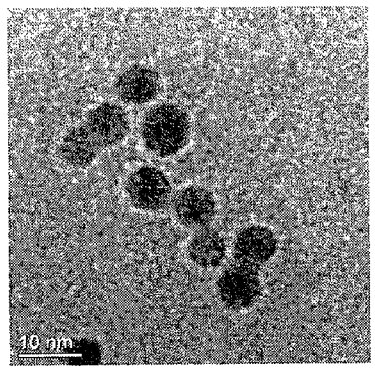
Figure 9A:
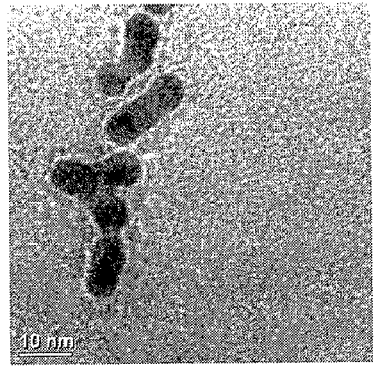

A schematic diagram of the process for forming Au NPs functionalized with $C_{10}$ lipids, 1,2-bis(11-mercaptoundecanoyl)-sn-glycero-3-phosphocholine), is shown in FIG. 9A. TEM images of the resulting structures are shown in FIGS. 9B and 9C. The hydrodynamic diameters of the unfunctionalized Au NPs (5 nm Au NPs) and the resulting functionalized structures (Au NP+$C_{10}$) were measured by dynamic light scattering and are shown in Table 4. As illustrated in the TEM images and in Table 4, the resulting structures had relatively uniform cross-sectional dimensions. The results also show that the size of the resulting structures can be controlled when using nanoparticles as a template for synthesis.

TABLE 4

Hydrodynamic diameters of unfunctionalized and functionalized structures using $C_{10}$ lipids

| Structure | Average (nm) | Std Dev (nm) |
|---|---|---|
| 5 nm Au NPs | 9.481 | 0.733 |
| Au NP + $C_{10}$ | 11.84 | 0.869 |

TABLE 4-continued

Hydrodynamic diameters of unfunctionalized and functionalized structures using $C_{10}$ lipids

| Structure | Average (nm) | Std Dev (nm) |
|---|---|---|
| Au NP + Apo + $C_{10}$ | 14.72 | 0.782 |
| Au NP + $C_{10}$ + $I_2$ | 18.46 | 0.701 |
| Au NP + Apo + $C_{10}$ + $I_2$ | 26.07 | N/A |

To synthesize structures including Apo-AI, the synthesis of $C_{10}$ or $C_{15}$ functionalized 5 nm Au NPs was performed as described above, but the 5 nm colloidal Au NP (2 mL, 80 nM) solution was first incubated with purified human apolipoprotein AI (18 microliters, 43.77 µM stock Apo-AI/2 mL Au NPs) and allowed to incubate at room temperature on a flat-top orbital shaker for 24 hours. The addition of $C_{10}$ and $C_{15}$ proceeded as above with subsequent centrifugation and purification steps.

Figure 9D:
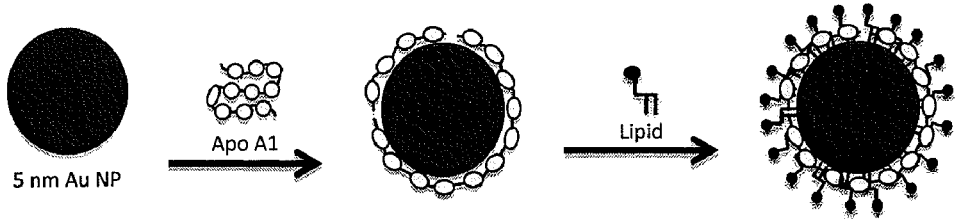
FIG. 9D shows a schematic diagram of a process for forming gold nanoparticles functionalized with lipids and Apo-AI, according to one set of embodiments.
Figure 9D:
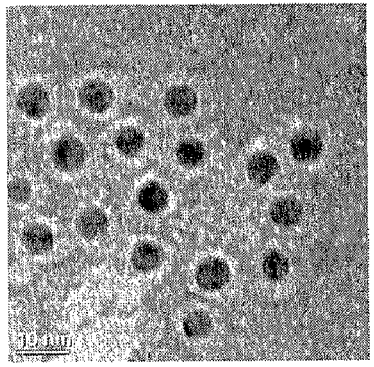
Figure 9D:
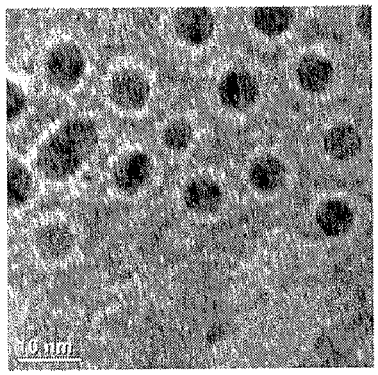

A schematic diagram of the process for forming Au NPs functionalized with Apo-$A_1$ and $C_{10}$ lipids, 1,2-bis(11-mercaptoundecanoyl)-sn-glycero-3-phosphocholine), is shown in FIG. 9D. TEM images of the resulting structures are shown in FIGS. 9E and 9F. The hydrodynamic diameters of the resulting structures (Au NP+Apo+$C_{10}$) were measured by dynamic light scattering and are shown in Table 4 above. As illustrated in the TEM images and in Table 4, the resulting structures had relatively uniform cross-sectional dimensions. The results also show that the size of the resulting structures can be controlled when using nanoparticles as a template for synthesis.

Figure 9G:
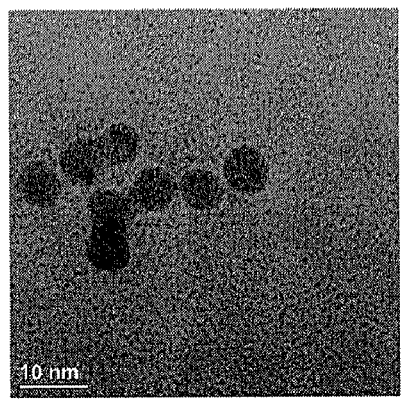
FIGS. 9G and 9H are TEM images showing gold nanoparticles functionalized with $C_{15}$ lipids, according to one set of embodiments.
Figure 9H:
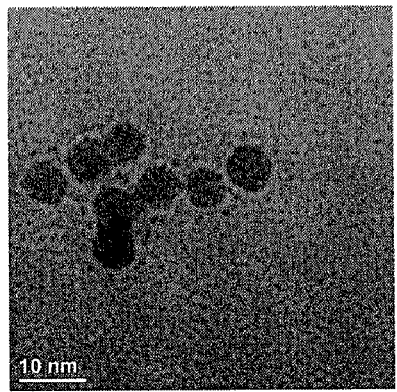

TEM images of Au NPs functionalized with $C_{15}$ lipids, 1,2-bis(16-mercaptohexadecanoyl)-sn-glycero-3-phosphocholine), are shown in FIGS. 9G and 9H. The hydrodynamic diameters of the unfunctionalized Au NPs (5 nm Au NPs) and the resulting structures (Au NP+Apo+$C_{15}$) were measured by dynamic light scattering and are shown in Table 5. As with the $C_{1-10}$-functionalized structures, the results shown in FIGS. 9G, 9H and in Table 5 demonstrate that the resulting structures (Au NP+Apo+$C_{15}$) had relatively uniform cross-sectional dimensions. The results also illustrate that the size of the resulting structures can be controlled when using nanoparticles as a template for synthesis.

TABLE 5

Hydrodynamic diameters of unfunctionalized and functionalized structures using $C_{15}$ lipids

| Structure | Average (nm) | Std Dev (nm) |
|---|---|---|
| 5 nm Au NPs | 9.481 | 0.733 |
| Au NP + $C_{15}$ | 12.29 | 3.51 |
| Au NP + Apo + $C_{15}$ | 13.17 | 0.852 |
| Au NP + $C_{15}$ + $I_2$ | 22.12 | N/A |
| Au NP + Apo + $C_{15}$ + $I_2$ | 383.77 | 165.35 |

Figure 9I:
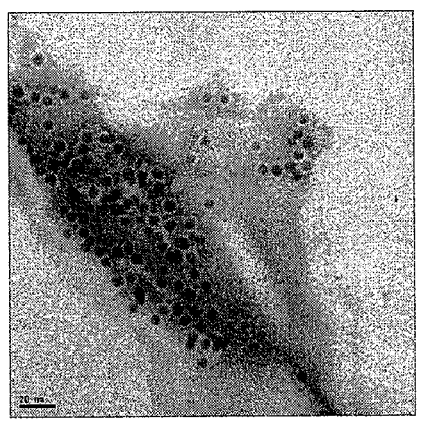
FIGS. 9I and 9J are TEM images showing gold nanoparticles functionalized with $C_{15}$ lipids and Apo-AI, according to one set of embodiments.
Figure 9J:
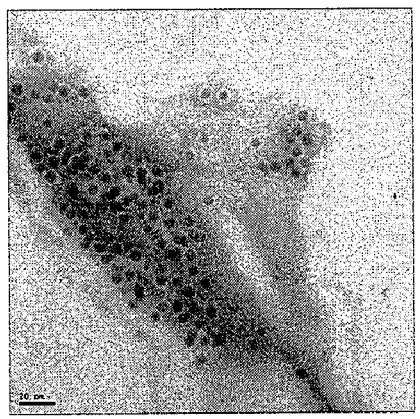

Au NPs functionalized with Apo-$A_1$ and $C_{15}$ lipids, 1,2-bis(16-mercaptohexadecanoyl)-sn-glycero-3-phosphocholine), are shown in FIGS. 9I and 9J. The hydrodynamic diameters of the resulting structures (Au NP+Apo+$C_{15}$) were measured by dynamic light scattering and are shown in Table 5 above.

All TEM images were obtained using samples that were prepared by depositing 5 µL of a concentrated solution of the structures of interest on a carbon-coated Cu TEM grid. The solution was allowed to set for 15 min. The grid was lightly blotted with filter paper to remove any remaining liquid, and then allowed to set for 5 min. 5 µL of 6% uranyl acetate was deposited on the grid and then allowed to set 10 min. The top of the grid was lightly touched with filter paper to remove any excess liquid, and allowed to set for 5 min.

All dynamic light scattering experiments were performed using disposable polystyrene cuvettes (DTS0012, Malvern), which were washed 1× in ethanol and 3× in nanopure $H_2O$. 1 mL of the structures of interest were slowly pipetted into the cuvette to avoid the production of bubbles. The surface of the cell was cleaned with a Kimwipe soaked in ethanol, and the cuvette was placed in a Malvern Zetasizer instrument according to manufacturer instructions. Measurements were performed using the 'manual' measurement function of the Malvern software and selecting the following parameters: RI 1.3, absorption 0.01, 25° C., Mark-Houwink parameters, 2 min equilibration time, 173° Backscatter (NIBS default), automatic measurement duration, 3 measurements, general purpose (normal resolution) analysis model. Using Excel software, 3 measurements taken by the Malvern are averaged and a standard deviation was calculated.

EXAMPLE 4

This example demonstrates the synthesis of stable self-assembled lipid layers on gold nanoparticles with $C_{10}$ and $C_{15}$ lipids, and the subsequent removal of gold metal from the functionalized nanoparticles to form at least partially hollow structures comprising a shell of lipid.

The methods described in Example 3 were followed to form gold nanoparticles functionalized with $C_{10}$ and $C_{15}$ lipids. To dissolve the gold metal (i.e., from Au(0) to $Au^+$ or $Au^{3+}$), 5 µL of 12 was added to ~20 µL of a concentrated solution of Au NP functionalized with the $C_{10}$ or $C_{15}$ lipids. The mixtures were vortexed and spun down using a centrifuge to collect the at least partially hollow structures.

The hydrodynamic diameters of functionalized Au NPs and the resulting structures after removal of gold metal were measured by dynamic light scattering and are shown in Tables 4 and 5 above.

Figure 9K:
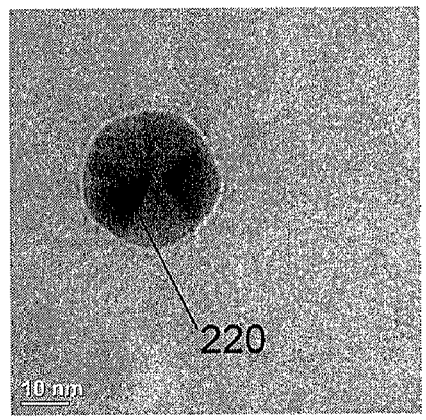
FIGS. 9K and 9L are TEM images showing at least partially hollow structures after gold nanoparticles functionalized with $C_{10}$ lipids have been treated with iodine, according to one set of embodiments.
Figure 9L:
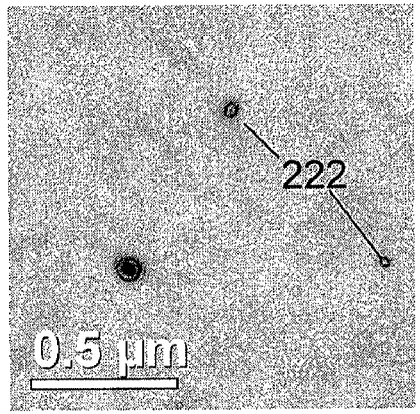

The nanoparticles in Table 4 were functionalized with $C_{10}$ lipids. The structures Au NP+$C_{10}$+$I_2$ included Au nanoparticles functionalized with $C_{10}$ lipids and then treated with iodine to remove the gold metal, forming at least partially hollow structures including a shell of lipid. A TEM image of a resulting structure after treatment with iodine is shown in FIG. 9K. The structure has a diameter of less than 30 nm and does not include Au(0) in its core, as demonstrated by UV-Vis experiments described below. As illustrated in FIG. 9K, the dark portions 220 near the center of the structure indicate that the center of the structure is electrodense. The electron density may be the result of the gold metal being oxidized to a salt, e.g., Au(0) to $Au^+$ and/or $Au^{3+}$. To remove the salt from the core, the structures may be subjected to mixing or vortexing to facilitate diffusion of the salt out of the core. FIG. 9L shows a TEM image of structures 222 having light centers, which indicate that the centers of the structures are not electrodense and that the salt has diffused out of the core to form at least partially hollow structures. Structures 222 had diameters of less than 30 nm. In other experiments, at least partially hollow structures having a diameter of less than 20 nm were formed (figures not shown).

At least partially hollow structures including $C_{10}$ and Apo-AI (Au NP+Apo+$C_{10}$±12) were made using a method similar to that described above for Au NP+$C_{10}$+$I_2$, except with the addition of Apo-AI. The hydrodynamic diameters of the structures after treatment with iodine are shown in Table 4.

Figure 10A:
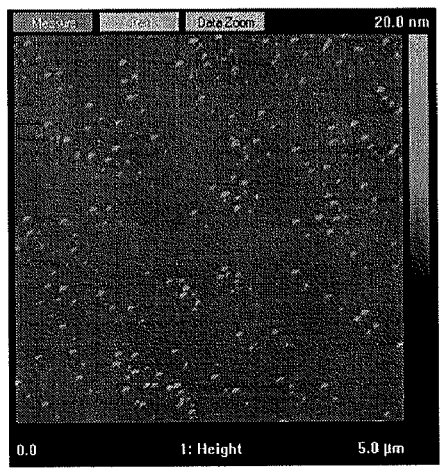
FIGS. 10A and 10B are AFM images of gold nanoparticles functionalized with $C_{10}$ lipids, according to one set of embodiments.
Figure 10B:
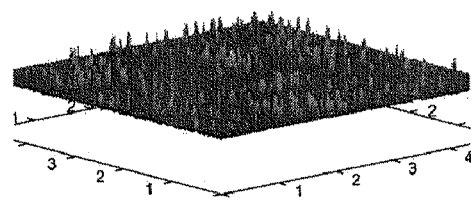
Figure 10C:
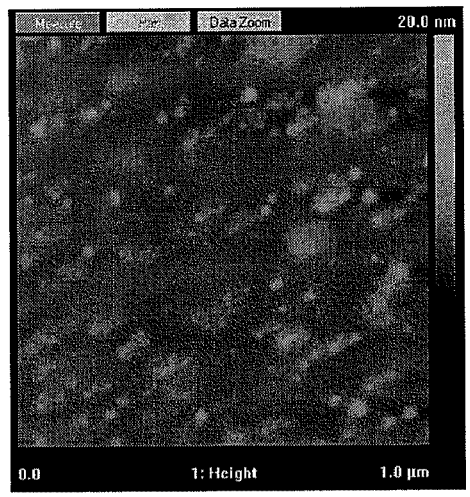
FIGS. 10C and 10D are AFM images of structures that are formed after treating $C_{1-10}$-functionalized gold nanoparticles with iodine, according to one set of embodiments.
Figure 10D:
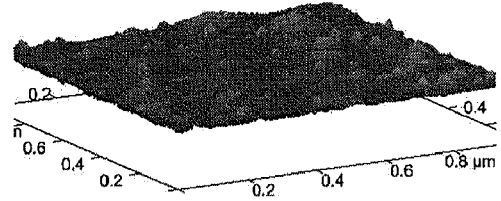

The structures formed before and after treatment with iodine were visualized by atomic force microscopy (AFM). The $C_{10}$ structures are shown in FIGS. 10A-10D. FIGS. 10A and 10B show structures that were formed prior to treatment with iodine; FIGS. 10C and 10D show the structures after treatment with iodine. FIGS. 10A and 10C are two-dimensional surface map AFM images showing that the resulting structures had dimensions in the nanometer range. FIGS. 10B and 10D are three-dimensional AFM surface images showing that the resulting structures had a height (e.g., diameter) of about 10 nm.

Figure 11A:
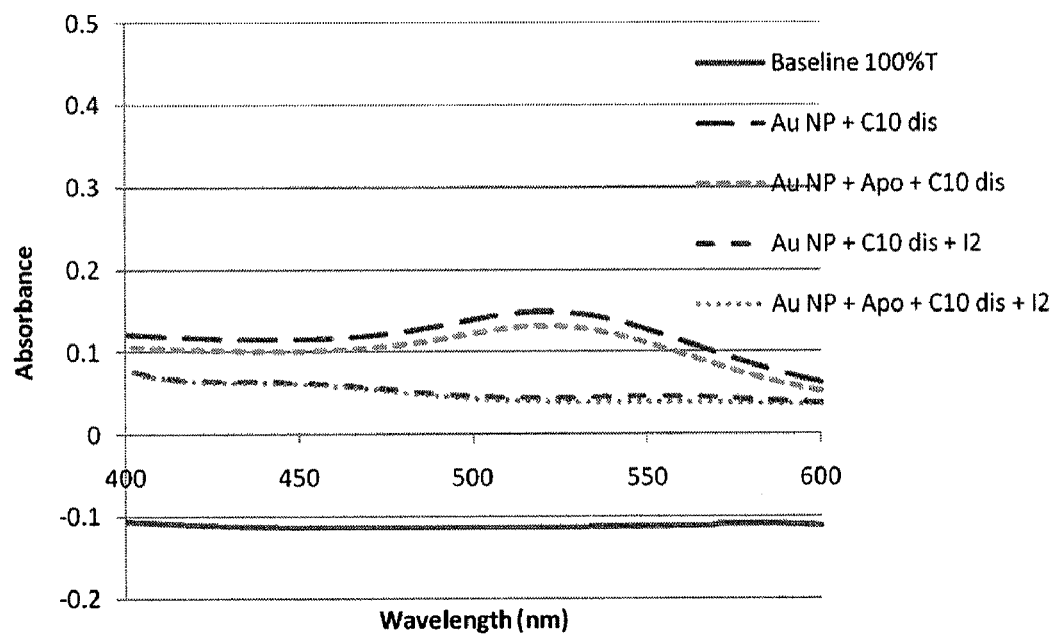
FIGS. 11A and 11B are UV-Vis plots of structures that are formed before and after treatment with iodine, according to one set of embodiments.

The structures before and after treatment with iodine were also characterized by UV-Vis measurements. As shown in FIG. 11A, the presence of the gold plasmon band at ~520 nm for the structures prior to treatment with iodine (Au NP+$C_{10}$, and Au NP+Apo+$C_{10}$) indicated that gold was present in the structures. The disappearance of the gold plasmon band at ~520 nm for the structures that were treated with iodine (Au NP+$C_{10}$+$I_2$, and Au NP+Apo+$C_{10}$+$I_2$) indicated that the gold metal dissolved after the iodine treatment.

The nanoparticles in Table 5 were functionalized with $C_{15}$ lipids. The structures Au NP+$C_{15}$±$I_2$ included Au nanoparticles functionalized with $C_{15}$ lipids and then treated with iodine to remove the gold metal, forming at least partially hollow structures including a shell of lipid. The structures at least partially hollow structures including $C_{15}$ and Apo-AI (Au NP+Apo+$C_{15}$+$I_2$) were made using a method similar to that described above for Au NP+$C_{15}$+$I_2$, except with the addition of Apo-AI. The hydrodynamic diameters of the structures after treatment with iodine are also shown in Table 5. Although Table 5 indicates that the resulting structures including $C_{15}$ and Apo-Al after treatment of iodine (Au NP+Apo+$C_{15}$+$I_2$) had an average hydrodynamic diameter of 383.77 nm, smaller structures having diameters of less than 30 nm were also synthesized in the process. The average diameter was calculated by taking the three most populated structure diameters in the sample, each obtained with an individual instrument run on the sample, and calculating an average based on the three measurements. In this particular experiment, because a range of sizes of the structures was synthesized and measured, a relatively high standard deviation of 165.35 was obtained. Without wishing to be bound by theory, the inventors believe that the relatively large diameters of the hollow structures may be due to the processing steps used, such as subjecting the structures to increased vortexing. The presence of Apo-AI in the shell may cause disruption of the packing of the $C_{15}$ lipids, thereby allowing the structures to expand upon vortexing. Additionally or alternatively, as the gold is dissolved, the structures may move to a less constrained arrangement that is 'swollen'. The large average hydrodymamic diameter may also be due to the instrument algorithms used for measuring particle size and for reporting particle hydrodynamic diameter. The size of the structures can be controlled by varying, among other parameters, the amount of vibration which may cause the lipid shell to expand or contract, and the particular components used to form the shell.

Figure 11B:
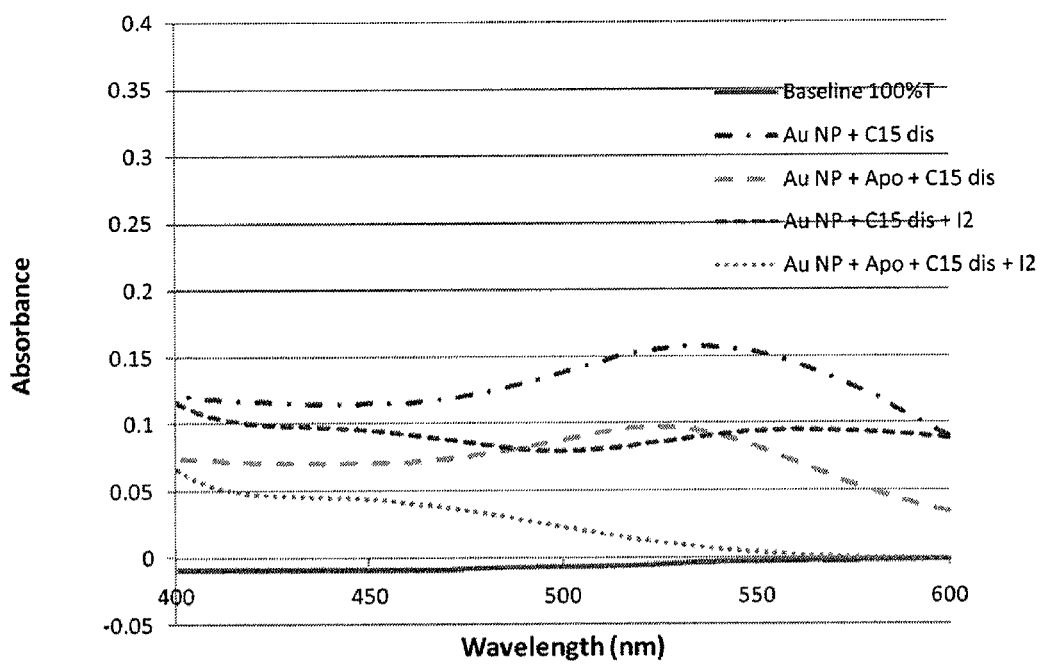

Similar to FIG. 11A, the plot shown in FIG. 11B shows that the ~520 plasmon peak disappeared after the structures were treated with iodine, illustrating the removal of gold metal from the structures.

This example shows that the size of structures that are at least partially hollow, and in which metal has been removed from the core of the structures, can be controlled when using nanoparticles as a template for synthesis.

EXAMPLE 5

This example demonstrates that the structures formed in Example 3 can be used to sequester cholesterol.

Figure 12:
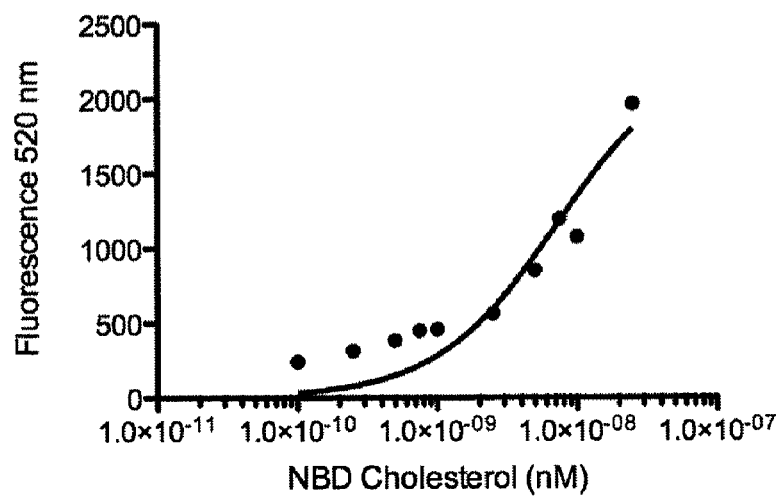
FIG. 12 is a plot showing binding of fluorescently-labeled cholesterol to structures functionalized with $C_{10}$ lipids, according to one set of embodiments.
Figure 13:
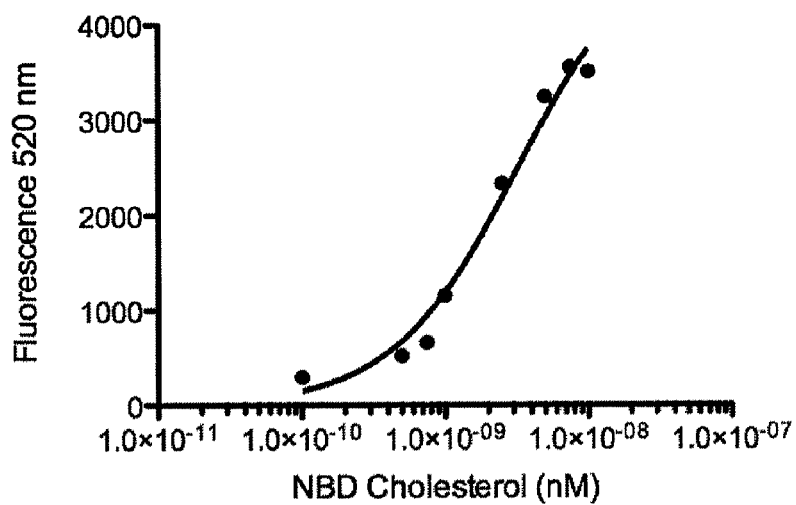
FIG. 13 is a plot showing binding of fluorescently-labeled cholesterol to structures functionalized with $C_{10}$ lipids and Apo-AI, according to one set of embodiments.

The structures Au NP+$C_{10}$ and Au NP+Apo+$C_{10}$ were exposed to solutions containing different concentrations of NBD cholesterol. NBD cholesterol has very little fluorescence in an aqueous environment. However, in a hydrophobic environment such as that found in a lipid monolayer, it becomes fluorescent. This fluorescence is observed as the cholesterol is absorbed by the lipid-functionalized structures. As shown in FIG. 12 with respect to the structure Au NP+$C_{10}$, and FIG. 13 with respect to the structure Au NP+Apo+$C_{10}$, when the structures are exposed to increasing concentrations of NBD cholesterol, a corresponding increase in fluorescence is observed. This demonstrates that more cholesterol is being adsorbed onto the surface of the structures with increasing concentrations of cholesterol.

$B_{max}$ and $K_d$ of the structures were determined using the method described in Example 2. A $B_{max}$=2320±436 and a $K_d$=7.212±3.151 nM was determined for the structures without Apo-AI (Au NPs+$C_{10}$). A $B_{max}$=4924±415.2 and a $K_d$=3.161±0.6848 nM was determined for the structures with Apo-AI (Au NPs+Apo+$C_{10}$). For the structures with Apo-AI, the $B_{max}$ doubles and the $K_d$ improves by a factor of 2 compared to structures that do not include the protein. This data demonstrates that cholesterol binding increases with the addition of Apo-AI. This data also shows that the ability of the structures to bind cholesterol can be varied by tailoring the surface chemistry of the structures.

Similar experiments were performed with structures that were functionalized with $C_{15}$ lipid (Au NP+$C_{15}$) and structures that were functionalized with both $C_{15}$ lipid and Apo-AI (Au NP+Apo+$C_{15}$). A $B_{max}$=2759±238.8 and a $K_d$=2.340±0.6622 nM was determined for the structures without Apo-AI (Au NPs+$C_{15}$). A $B_{max}$=2245±146.3 and a $K_d$=0.1104±0.05136 nM was determined for the structures with Apo-AI (Au NPs+Apo+$C_{15}$). The $B_{max}$ for the structures with and without Apo-AI were similar, but the experiments show that the addition of Apo-AI results in a lower $K_d$, indicating improvement in cholesterol binding by a factor of 20.

This example shows that the surface chemistry of the structures described herein can be tailored to improve cholesterol binding by, for example, choosing an appropriate surface component (e.g., $C_{15}$ vs. $C_{10}$ lipids) and/or proteins (e.g., Apo-AI).

EXAMPLE 6

This example illustrates a method for synthesizing structures described herein by a single-phase synthesis. Specifically, lipid-functionalized gold nanoparticles were synthesized in ethanol/water.

Per 1 mL synthesis, 100 µL 1,2-dipalmitoyl-sn-glycerophosphoethanolamine-N-[3-(2-pyridyldithio)propionate] (sodium salt) (Disulfide lipid, Avanti Polar Lipids) in ethanol at a concentration of 1 mM was added to an Eppendorf tube and mixed with 100 µL of 1,2-dipalmitoyl-sn-glycero-3-phosphocholine (DPPC, Avanti Polar Lipids) in ethanol, also at a concentration of 1 mM. This mixture is vortexed to mix thoroughly. 1 mL of 5 nm Au NPs (~83 nM, Ted Pella) in water was then added to the mixture, and vortexed once more, followed by ~5 min of sonication in a Branson 2510 sonication bath, and ~30 min of shaking on an Eppendorf Thermomixer at 1400 rpm. In order to isolate the lipid-functionalized Au NPs, the mixture was centrifuged 3× in aliquots of 250 µL for 45 min at 15000 rpm each time. After each spin the supernatant was removed and discarded, and the lipid-functionalized Au NPs were re-suspended in the same volume nanopure $H_2O$. After the final spin, aliquots were recombined and the lipid-functionalized Au NPs were re-suspended in $H_2O$ or PBS(1×). In a final functionalization step, 11.4 µL apolipoprotein A1 (Apo-AI[human], Biodesign, 35.3 µM) was added to the lipid-functionalized Au NPs. The mixture was vortexed, and allowed to mix overnight on an Eppendorf Thermomixer at 1400 rpm. The mixture was again centrifuged 3× (45 min at 15000 rpm each) in aliquots of 250 µL, re-suspending in the same volume $H_2O$ or PBS (1×) in between spins. Following the final spin, aliquots are recombined, and the HDL-Au NPs are re-suspended in $H_2O$ or PBS (1×) to the desired concentration.

Structures were functionalized with Apo-AI (Au+DiS+ DPPC+APO) using the method described in Example 3.

Figure 14:
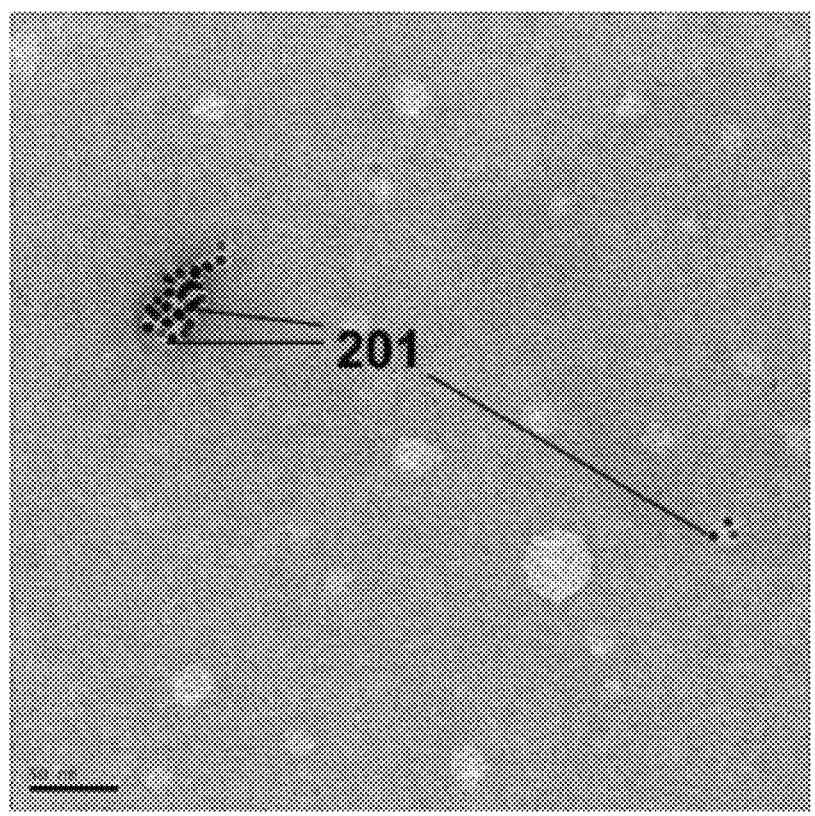
FIG. 14 shows structures that were formed using a one-phase synthesis, according to one set of embodiments.

To characterize the resulting structures 201, dynamic light scattering measurements were performed. The results are shown in Table 9. The structures 201 were also characterized by electron microscopy, as shown in FIG. 14.

TABLE 6

Hydrodynamic diameters of functionalized (Au + DiS + DPPC, Au + DiS + DPPC + APO) and unfunctionalized (5 nm AU NP) gold nanoparticles.

|  | Ave. Diameter (nm) | SD (nm) |
| --- | --- | --- |
| 5 nm Au NP | 8.3 | 3.5 |
| Au + DiS + DPPC | 18.3 | 1.1 |
| Au + DiS + DPPC + APO | 16.5 | 1.3 |

The same protocols described above were also performed using fluorescently-labeled DPPC and fluorescently-labeled APO. On average, the structures included 26.23 fluorescently labeled DPPC molecules in the outer portion of the shell (approximately half of the total phospholipid content since a bilayer was formed) and 0.76 Apo-AI molecules in the outer portion of the shell.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A structure comprising:
   a nanostructure core comprising an inorganic material;
   a shell comprising a lipid bilayer surrounding and attached to the nanostructure core, the shell having an inner surface and an outer surface; and
   an apolipoprotein bound to at least the outer surface of the shell.

2. A kit for treating or managing a disease or bodily condition associated with abnormal lipid levels, comprising:
   a composition comprising a plurality of structures, each structure comprising a nanostructure core comprising an inorganic material, a shell comprising a lipid bilayer surrounding and attached to the nanostructure core, and an apolipoprotein bound to at least the outer surface of the shell; and
   instructions for use of the composition for treating or managing a disease or bodily condition associated with abnormal lipid levels.

3. The kit as in claim 2, wherein the disease or bodily condition is associated with abnormally high lipid levels.

4. The kit as in claim 2, wherein the disease or bodily condition comprises atherosclerosis.

5. The structure as in claim 1, wherein the shell comprises 1 to 6 apolipoproteins.

6. The structure as in claim 1, wherein the apolipoprotein is apolipoprotein A-I, apolipoprotein A-II, or apolipoprotein E.

7. The structure as in claim 1, wherein the structure has a largest cross-sectional dimension of less than or equal to about 50 nm.

8. The structure as in claim 1, wherein the nanostructure core has a largest cross-sectional dimension of less than or equal to about 50 nm.

9. The structure as in claim 1, wherein at least a portion of the lipid bilayer is physisorbed to the nanostructure core.

10. The structure as in claim 1, wherein the lipid bilayer is attached to the nanostructure core through a thiol-metal bond.

11. The structure as in claim 1, wherein the lipid bilayer comprises a phospholipid.

12. The structure as in claim 1, wherein the lipid bilayer comprises 50-200 phospholipids.

13. The structure as in claim 1, wherein the nanostructure core is formed of a metal.

14. The structure as in claim 13, wherein the metal is gold.

15. The structure as in claim 1, wherein the nanostructure core is formed of a semiconductor.

16. The structure as in claim 1, wherein the structure comprises lecithin-cholesterol acyltransferase, bound to the lipid bilayer.

17. The structure as in claim 1, wherein the nanostructure core has a largest cross-sectional dimension of less than or equal to about 30 nm.

18. The structure as in claim 1, wherein the nanostructure core comprises a polymer.

19. The structure as in claim 1, wherein the nanostructure core is substantially spherical.

20. The structure as in claim 1, wherein the structure comprises a small molecule, bound to the lipid bilayer, that targets a specific cell surface marker.

21. The structure as in claim 1, comprising esterified cholesterol bound to at least a portion of the shell.

22. The structure as in claim 1, wherein at least a portion of the lipid bilayer is covalently bound to the nanostructure core.

23. The structure as in claim 1, wherein the structure comprises an enzyme bound to the lipid bilayer.

24. The structure as in claim 1, wherein at least a portion of the apoliporprotein is embedded in the shell.

25. The structure as in claim 1, wherein at least a portion of the apolipoprotein is bound to the nanostructure core.

26. The structure as in claim 1, wherein at least a portion of the apolipoprotein is bound to the outer surface of the shell by covalent bonding.

27. The structure as in claim 1, wherein the structure comprises a contrast agent.

28. The structure as in claim 1, wherein the structure comprises a bioactive agent including one or more of an anti-inflammatory, a nucleic acid a chemotherapeutic, and a cholesterol-lowering agent.

29. A pharmaceutical composition comprising the structure of claim 1, wherein the pharmaceutical composition further comprises one or more pharmaceutically acceptable carriers, additives, and/or diluents.

30. The kit as in claim 2, wherein the apolipoprotein is apolipoprotein A-I, apolipoprotein A-II or apolipoprotein E.

31. The kit as in claim 2, wherein the structure has a largest cross-sectional dimension of less than or equal to about 50 nm.

32. The kit as in claim 2, wherein the nanostructure core has a largest cross-sectional dimension of less than or equal to about 30 nm.

33. The kit as in claim 2, wherein the nanostructure core comprises a polymer.

34. The kit as in claim 2, wherein at least a portion of the lipid bilayer is physisorbed to the nanostructure core.

35. The kit as in claim 2, wherein at least a portion of the lipid bilayer is attached to the nanostructure core through a thiol-metal bond.

36. The kit as in claim 2, wherein the lipid bilayer comprises a phospholipid.

37. The kit as in claim 2, wherein the lipid bilayer comprises 50-200 phospholipids.

38. The kit as in claim 2, wherein the nanostructure core is formed of a metal.

39. The kit as in claim 38, wherein the metal is gold.

40. The kit as in claim 2, wherein the nanostructure core is formed of a semiconductor.

41. The kit as in claim 2, wherein the structure comprises lecithin-cholesterol acyltransferase.

42. The kit as in claim 2, wherein at least a portion of the apolipoprotein is embedded in the shell.

43. The kit as in claim 2, wherein at least a portion of the apolipoprotein is bound to the nanostructure core.

44. The kit as in claim 2, wherein the structure comprises a contrast agent.

45. The kit as in claim 2, wherein the structure comprises a bioactive agent including one or more of an anti-inflammatory, a nucleic acid, a chemotherapeutic, and a cholesterol-lowering agent.

* * * * *

UNITED STATES PATENT AND TRADEMARK OFFICE
CERTIFICATE OF CORRECTION

| | |
|---|---|
| PATENT NO. | : 8,323,686 B2 |
| APPLICATION NO. | : 12/429560 |
| DATED | : December 4, 2012 |
| INVENTOR(S) | : Chad A. Mirkin et al. |

It is certified that error appears in the above-identified patent and that said Letters Patent is hereby corrected as shown below:

In the Claims:

At column 40, claim 24, Line 22-23, please replace "The structure as in claim 1, wherein at least a portion of the apoliporprotein is embedded in the shell." with -- The structure as in claim 1, wherein at least a portion of the apolipoprotein is embedded in the shell. --

At column 40, claim 28, Line 31-34, please replace "The structure as in claim 1, wherein the structure comprises a bioactive agent including one or more of an anti-inflammatory, a nucleic acid a chemotherapeutic, and a cholesterol-lowering agent." with -- The structure as in claim 1, wherein the structure comprises a bioactive agent including one or more of an anti-inflammatory, a nucleic acid, a chemotherapeutic, and a cholesterol-lowering agent. --

Signed and Sealed this
Fourth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,323,686 B2
APPLICATION NO. : 12/429560
DATED : December 4, 2012
INVENTOR(S) : Chad A. Mirkin et al.

It is certified that error appears in the above-identified patent and that said Letters Patent is hereby corrected as shown below:

In the Specification:

At column 1, line 23 please replace the FEDERALLY SPONSORED RESEARCH paragraph "This invention was made with U.S. government support under NIH (NCI/CCNE) grant No. U54 CA 119341 and NIH Pioneer Award No. 5 DP1 OD000285. The government has certain rights to this invention." with --This invention was made with government support under grant numbers CA119341 and 5 DP1 OD00285 awarded by the National Institutes of Health and grant number EEC-0647560 awarded by the National Science Foundation. The government has certain rights in the invention.--

Signed and Sealed this
Fifteenth Day of April, 2014

Michelle K. Lee
*Deputy Director of the United States Patent and Trademark Office*